US011473045B2

(12) United States Patent
Guenat et al.

(10) Patent No.: US 11,473,045 B2
(45) Date of Patent: Oct. 18, 2022

(54) DEVICE FOR IN-VITRO MODELLING IN-VIVO TISSUES OF ORGANS

(71) Applicant: Universität Bern, Bern (CH)

(72) Inventors: Olivier Thierry Guenat, Bern (CH); Marcel Felder, Bern (CH); Andreas Stucki, Bern (CH); Janick Daniel Stucki, Bern (CH); Thomas Geiser, Hinterkappelen (CH)

(73) Assignee: Universität Bern, Bern (CH)

( * ) Notice: Subject to any disclaimer, the term of this patent is extended or adjusted under 35 U.S.C. 154(b) by 186 days.

(21) Appl. No.: 16/051,201

(22) Filed: Jul. 31, 2018

(65) Prior Publication Data

US 2018/0355299 A1 Dec. 13, 2018

Related U.S. Application Data

(63) Continuation of application No. 14/916,026, filed as application No. PCT/EP2014/068921 on Sep. 5, 2014, now Pat. No. 10,066,198.

(30) Foreign Application Priority Data

Sep. 5, 2013 (EP) .................................... 13183063

(51) Int. Cl.
*C12M 3/00* (2006.01)
*C12M 1/12* (2006.01)
(Continued)

(52) U.S. Cl.
CPC ............ *C12M 21/08* (2013.01); *C12M 25/02* (2013.01); *C12M 25/04* (2013.01); *C12M 29/10* (2013.01);
(Continued)

(58) Field of Classification Search
CPC ...... C12M 21/08; C12M 25/02; C12M 25/04; C12M 29/10; C12M 35/04; C12M 35/08; C12M 41/40
See application file for complete search history.

(56) References Cited

U.S. PATENT DOCUMENTS 4,789,601 A   12/1988  Banes
5,470,743 A   11/1995  Mussi et al.
(Continued)

FOREIGN PATENT DOCUMENTS

WO   2010/009307 A2   1/2010
WO   2015/166625 A1   11/2015

OTHER PUBLICATIONS

European Search Report issued in European Patent Application No. EP 20 15 2403 dated Apr. 30, 2020.
(Continued)

*Primary Examiner* — Lydia Edwards
(74) *Attorney, Agent, or Firm* — Hoffmann & Baron, LLP

(57) ABSTRACT

A device for in-vitro modelling in-vivo tissues of organs that includes a first body portion with at least one access chamber, a second body portion with at least one culturing chamber, and a culturing membrane dividing the at least one access chamber from the culturing chamber. The device further includes a third body portion with at least one actuation chamber having at least one limitation cavity, and an actuation membrane dividing the at least one culturing chamber from the at least one actuation chamber. With the device, a robust actuation system can be provided that does not depend on the mechanical properties of the actuation membrane material, nor on the pressure, and that allows to mimic three-dimensional deformations of the tissue, in particular of lung alveoli.

13 Claims, 14 Drawing Sheets

(51) Int. Cl.
   *C12M 1/00*    (2006.01)
   *C12M 1/42*    (2006.01)
   *C12M 1/34*    (2006.01)

(52) U.S. Cl.
   CPC ............ *C12M 35/04* (2013.01); *C12M 35/08* (2013.01); *C12M 41/40* (2013.01)

(56) References Cited

U.S. PATENT DOCUMENTS

| | | |
|---|---|---|
| 2006/0019375 A1 | 1/2006 | Seidl et al. |
| 2006/0270023 A1 | 11/2006 | LeDuc et al. |
| 2009/0088342 A1 | 4/2009 | Moraes et al. |
| 2010/0233799 A1 | 9/2010 | Takayama et al. |
| 2011/0250585 A1 | 10/2011 | Ingber et al. |
| 2014/0038279 A1* | 2/2014 | Ingber .................... C12M 23/38 435/297.2 |
| 2017/0044480 A1 | 2/2017 | Toyoda et al. |

OTHER PUBLICATIONS

Written Opinion of the International Searching Authority issued in International Application No. PCT/EP2014/068921 dated Nov. 4, 2014.

* cited by examiner

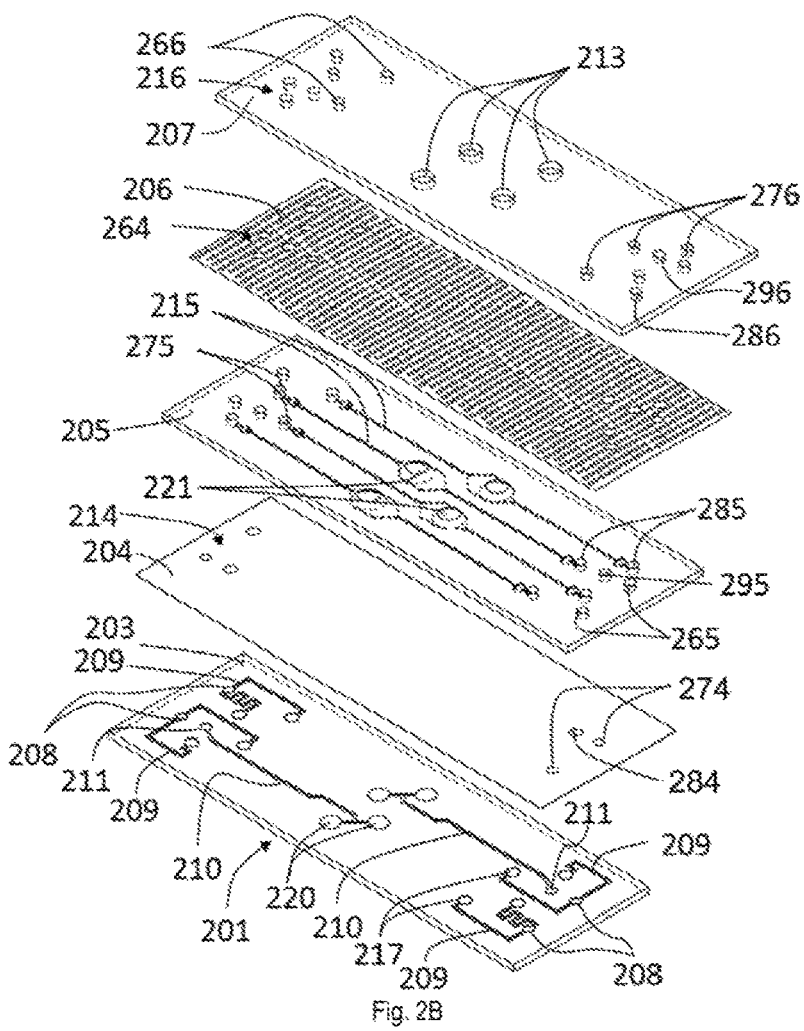
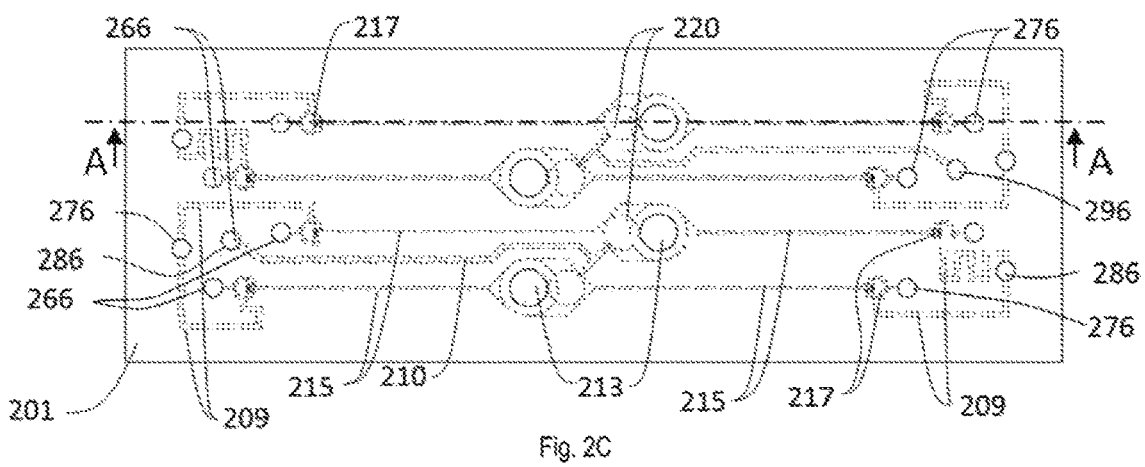
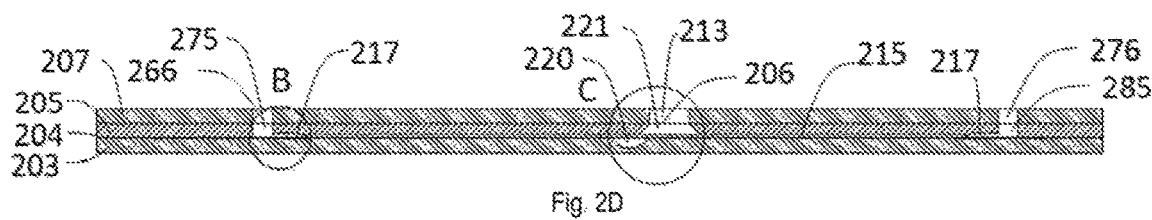
Fig. 2B
Fig. 2C
Fig. 2D

DEVICE FOR IN-VITRO MODELLING IN-VIVO TISSUES OF ORGANS

CROSS-REFERENCE TO RELATED APPLICATIONS

This application is a continuation of U.S. patent application Ser. No. 14/916,026, filed 2 Mar. 2016, which is the U.S. National Phase of International Patent Application No. PCT/EP2014/068921, filed on 5 Sep. 2014, which claims benefit of European Patent Application No. 13183063.0, filed on 5 Sep. 2013, the contents of which are incorporated herein by reference in their entirety.

TECHNICAL FIELD

The present invention relates to a device for in-vitro modelling in-vivo tissues of organs. More specifically, the device includes a first body portion with at least one access chamber, a second body portion with at least one culturing chamber, and a culturing membrane dividing the at least one access chamber from the culturing chamber, which device can be used for in-vitro modelling in-vivo tissues of organs.

BACKGROUND ART

The pharmaceutical sector is currently experiencing efforts in rethinking the way research and development can be performed more efficiently. One important issue that needs to be addressed is the lack of efficient and reproducible drug discovery models that are able to predict toxicity and efficiency of compounds in humans prior to launch of expensive clinical trials.

Similarly, chemical companies as well as public and regulation authorities are looking for alternative in-vitro methods to animal testing. The latter poorly predict the human response, are ethically controversial and costly. However, the absence of efficient and reproducible in-vitro models able to predict the toxicity of chemical compounds in humans is one hurdle that needs to be tackled in toxicology testing.

This is particularly true for in-vitro models of the lung, due to the complex cellular microenvironment present in the lower airways where the gas exchange takes place. The in-vivo conditions of the lungs, such as air-liquid interface, respiratory movements, shear stresses induced by liquids over the epithelial layer and at the endothelium, etc. are particularly complex, which is a reason why accurate in-vitro alveolar models do not exist to date.

Known in-vitro models of the lung, such as transwell systems, can reproduce tissue interfaces between alveoli and vascular endothelium, but neither the mechanical processes of physiological breathing nor the shear stress induced by the blood stream, nor the removal of the soluble products and the waste products excreted by the cells. In addition, transwell membrane thicknesses are typically between ten and twenty micrometers, which is about one to three orders of magnitude larger than the in-vivo dimension. This can importantly hamper the epithelial endothelial signalling.

In this context, research platforms based on microfluidic technologies are currently emerging and have the potential to improve in-vitro model accuracy and experimental efficiency. For example, microfabricated bio-artificial lung models have only been reported in the past three years.

In WO 2010/009307 A2 a breathing lung-on-chip is described using a co-culture of epithelial/endothelial cells. This lung-on-chip is made of two superposed microchannels separated by a thin porous and stretchable membrane made of Polydimethylsiloxane (PDMS). This membrane, on which epithelial and endothelial cells are cultured, is cyclically linearly stretched by varying the pressure in adjacent channels, which allows the deformation of the walls of the microchannels on which the thin porous membrane is attached.

However, the actuation principle shown in WO2010/009307 A2 suffers important limitations. Indeed, the accuracy of the stress level of the thin membrane directly depends on the amplitude of the deflection of the internal channel walls, which in turn is a function of a number of parameters, in particular, the mechanical properties and the geometry of the walls material and the actuation pressure, which all need to be accurately controlled. In addition, the construction of the device based on the assembly of two parts—the top and the bottom parts—between which the thin membrane is sandwiched requires an accurate alignment to guarantee the batch to batch reproducibility of the mechanical properties of the channel walls.

At least these factors do not allow the precise control of the stretching level of the thin membrane and ultimately of the cells that are cultured on this membrane. Therefore, the fabrication processes of the device must be extremely accurate, which increases the production costs and/or may require a costly calibration of the stress in the membrane in function of the applied pressure for each device. Furthermore, several aspects of this device only approximately reproduce the basement membrane of the lung alveoli and its deformation. Indeed, the unidirectional stretching generated by the adjacent channels of this device does not correspond to the three-directional stretching that takes place in the human lung. In-vivo, the respiratory movements are the result of the contraction of the diaphragm that pulls the cavity of the lung, causing air to enter in the lungs. Also, the membrane integrated in the lung-on-chip described in WO2010/009307 A2 is comparably thick, i.e., about ten micrometers, as compared to the thickness of the basement of the lung alveolar membrane, which is between 200 and 500 nanometers.

In US 2010/0233799 A1 another example of a microfluidic lung-on-chip with a stretchable membrane is shown. Thereby, a device includes a PDMS membrane on which epithelial cells are cultured. In order to investigate the mechanical stresses that typically occur in ventilated lungs, a pin exerts a mechanical force on the membrane.

However, for being suitable to such pin exertion, the membrane has to be robust and is in the device of US 2010/0233799 A1 about 100 micrometers thick. The shown device is not equipped with a porous membrane and thus does not allow mimicking the complexity of the alveolar membrane by reproducing the air-blood barrier. Further, the device does not allow for the culture of cells at the side of the membrane where the pin pushes to deform the membrane since the direct contact of the pin with the membrane would squeeze the cells and damage them. This means that this system does not allow mimicking the co-culture system typical to in-vitro barriers, even if one would integrate a porous membrane.

An additional limitation of the system described in US 2010/0233799 A1, also due to the direct contact of the pin against the membrane, is the obvious absence of space between the pin and the membrane. This prevents providing sufficient space for physiological medium, and as a consequence, cells could not be perfused. Since no physiological solution can be provided to the cells from the bottom of the membrane, the physiological medium needs to be provided from the top of the membrane where the cells are cultured, meaning that no air-liquid interface (ALI) condition can be set up in this system.

Another downside of the system of US 2010/0233799 A1 is that the observation of the cells from the bottom of the chip is not possible with a non-transparent pin. And even if the pin were transparent, the images would still be distorted due to the curvature of the pin, and thus would have to be corrected, e.g., by a specific software, in order to be appropriate.

Still further, the system of US 2010/0233799 A1 only allows stretching the membrane in one outward direction, whereas in the lung, this direction is only true for the endothelial cells. Also, the stretch profile in the system of US 2010/0233799 A1 is very heterogeneous. In particular, only the membrane in the middle will adapt to the structure of the pin, whereas the membrane in the periphery does not adapt. This results in different stretch profiles between the middle of the membrane and the periphery of the membrane and, in addition, the alveoli in the lung are stretched similar to an expanding sphere. This means that the radius of the sphere changes constantly wherein, in this system, the radius is given by the shape of the pin.

Therefore, there is a need for a device for in-vitro modelling tissues of organs that allows to, e.g., cyclically stretch cells in predefined and varying extent and/or direction thus making it possible to mimic three-dimensional deformation of the tissue such as the lung alveoli.

SUMMARY

This need is settled by a device for in-vitro modelling in-vivo tissues of organs as described herein.

In particular, the gist of the invention is the following: A device for in-vitro modelling in-vivo tissues of organs includes a first body portion with at least one access chamber, a second body portion with at least one culturing chamber, and a culturing membrane dividing the at least one access chamber from the culturing chamber. The device further includes a third body portion with at least one actuation chamber having at least one limitation cavity, and an actuation membrane dividing the at least one culturing chamber from the at least one actuation chamber.

The term "modelling in-vivo tissues" in the context of the invention can relate to modelling in-vivo conditions of tissues of the organs, such as, e.g., the lung, and more particularly to tissue interfaces, such as tissue interfaces between alveoli and vascular endothelium. The first, second, and third body portions can be formed as distinct physical units, which can be mounted together, as combined physical units, such as the first and second body portions being one physical unit, and the third body portion being a second physical unit, or as one single physical unit. The first, second, and third body portions can, e.g., be plate-shaped. In some embodiments, the at least one access chamber can also be used for culturing such that it is a combined access-culturing chamber. The culturing membrane can be porous, i.e., completely or partially porous, or non-porous. It can further be comparably thin and flexible and can be coatable with cells on one or both its sides in order to create an in-vitro barrier, similar to in-vivo barriers, such as the air-blood barrier in the lungs. The term "comparably thin" in this context can relate to a thickness of between about 10 nanometers (nm) to about 20 micrometers (µm), or between about 20 nanometers to about 10 micrometers, or between about 200 nanometers and about 5 micrometers. The size of pores of the culturing membrane can be between about 0.4 micrometers to about 12 micrometers, and can be about 3 micrometers. The density of the pores can be between about 10'000 and about 100'000'000 pores/cm$^2$ and can be about 800'000 pores/cm$^2$.

The culturing membrane can have a thickness in a range of about 100 nm to 10 µm, in a range of about 200 nm to 3 µm, or in a range of about 500 nm to 1 µm. In some embodiments, e.g., where the access chamber and the culturing chamber are arranged on the same level, the culturing membrane and the actuation membrane can be the same, i.e., being one single physical unit. The actuation chamber can have a single limitation cavity or plural limitation cavities. Also, there can be plural actuation chambers, each having a single limitation cavity or plural limitation cavities.

The culturing membrane dividing the at least one access chamber from the culturing chamber can be implemented by arranging the access chamber and the culturing chamber directly adjacent to each other, and the culturing membrane between the access chamber and the culturing chamber. Alternatively, the culturing membrane can be implemented by indirectly connecting the access chamber and the culturing chamber via at least one further chamber, such as a channel or microchannel or the like, and arranging the culturing membrane either in the at least one further chamber, adjacent to the at least one further chamber and the culturing chamber or adjacent to the at least one further chamber and the access chamber. The culturing membrane can be used for culturing cells on one or both of its surfaces. The cells cultured on the culturing membrane can be perfused either continuously or intermittently, or can be stationary grown.

Further, on one or both surfaces of the culturing membrane, various types of cells can be implanted or grown. Such cells can include any procariotic and eucariotic cell type from a multicellular structure, including nematodes, amoebas, and bacteria, up to mammals, such as humans. Cell types implanted or grown on the culturing membrane of the device depend on the type of organ or organ function one wishes to mimic and the tissues that include those organs. Also, various stem cells, such as bone marrow cells, induced adult stem cells, embryonic stem cells, or stem cells isolated from adult tissues can be co-cultured on either or both sides of the culturing membrane. Using different culture media in the culturing and/or access chambers feeding each layer of cells, one can allow different differentiation cues to reach the stem cell layers, thus differentiating the cells to different cell types. One can also mix cell types on the same side of the culturing membrane to create co-cultures of different cells without membrane separation.

The actuation membrane dividing the at least one culturing chamber from the at least one actuation chamber can be implemented by arranging the actuation chamber, or particularly its limitation cavity, and the culturing chamber directly adjacent to each other and the actuation membrane between the actuation chamber and the culturing chamber. Alternatively, it can be implemented by indirectly connecting the actuation chamber and the culturing chamber via at least one further chamber, such as, a channel or a microchannel or the like, and arranging the actuation membrane either in the at least one further chamber, adjacent to the at least one further chamber and the culturing chamber, or adjacent to the at least one further chamber and the actuation chamber.

In use of the device according to the invention, the culturing membrane can be deflected by adjusting the pressure in the actuation chamber. In particular, adjusting the pressure inside the actuation chamber can cause the actuation membrane to be deflected, depending on the pressure, either into (decreasing pressure) or out of (increasing pressure) the actuation chamber, i.e., either negatively or positively. Thus, the pressure inside the culturing chamber can also be changed such that the culturing membrane deflects accordingly into or out of the culturing chamber. This effect can particularly be present if the culturing chamber is partially or fully filled with a comparably incompressible medium or fluid. Adjusting the pressure inside the actuation chamber allows for applying cyclic, predefined deflection and also changing three-dimensional deflection of the culturing membrane in correspondence with the deflection of the actuation membrane. Thus, it can be used for stretching of the cells cultured on the culturing membrane. In various embodiments, the actuation membrane can also be deflected by other means than by pressure changes. For example, such deflection can be achieved by a magnetic force, i.e., by the addition of magnetic materials either in the membrane or outside of the membrane.

Furthermore, providing the actuation chamber with one or more limitation cavities allows for limiting the deflection of the actuation membrane and, in correspondence therewith, also of the culturing membrane. This can make the operation and setup of the device comparably easy since the deflection can be limited independent from the type and material of the culturing membrane. In other words, the deflection of the actuation membrane, which can correspond to the desired deflection of the culturing membrane or in-vitro barrier, can be geometrically limited by the design of the limitation cavity. As a result, the stretching level of the cells cultured on the culturing membrane can be kept constant regardless of the cell culture confluence on the culturing membrane, of the presence of an air-liquid or a liquid-liquid interface, and to a certain extent to the mechanical properties of the culturing membrane. By restraining the deflection of the actuation membrane, the batch to batch variations of the culturing membrane material's visco-elastic properties and the variation of the actuation membrane geometry can be circumvented to a large extent. As a result, a required actuation pressure does not mandatorily need to be accurately controlled, which can provide for a calibration free actuation. Also, this set-up allows to indirectly create small and accurate pressures that are required to stretch the cells cultured on the culturing membrane, by deflecting, e.g., the thicker actuation membrane with a higher pressure.

Therefore, with the device according to the invention, a robust actuation system can be provided that does not depend on the mechanical properties of the actuation membrane material, nor on the pressure, and that allows to mimic three-dimensional deformations of the tissue, in particular, lung alveoli.

When using the device according to the invention for culturing cells on the culturing membrane, the cellular responses to various environmental impacts can be monitored using various systems that can be combined with the device. For example, one can monitor changes in pH using well known sensors. Or, one can sample the cellular supernatant continuously or periodically for measurement of the concentration changes of the cellular secreted factors (growth factors, cytokines, chemokines) or one can sample cells, continuously or periodically for measurement of changes in gene transcription or changes in cellular biochemistry or structural organization. For example, one can measure reactive oxygen species (ROS) that are a sign of cellular stress. One can also measure the trans-epithelial electrical resistance (TEER) to monitor the confluence and/or the permeability of the in-vitro barrier. One can also subject the "tissue" grown on the culturing membrane to microscopic analysis, immunohistochemical analysis, in situ hybridization analysis, or typical pathological analysis using staining, such as hematoxylin and eosin staining Samples for these analyses can be carried out in real-time, or taken after an experiment or by taking small biopsies at different stages during a study or an experiment. Further, one can subject the cells grown on the membrane to other cells, such as immune system cells or bacterial cells, to antibodies or antibody-directed cells, for example to target specific cellular receptors. One can expose the cells to viruses or other particles. To assist in detection of movement of externally supplied substances, such as cells, viruses, particles or proteins, one can naturally label them using typical means such as radioactive or fluorescent labels. For example, cells can be grown, cultured and analysed using the device according to the invention for 1, 2, 3, 4, 5, 6 or 7 days, between at least 1-2 weeks, and even over 2 weeks.

In a non-limiting example embodiment, the device according to the invention is configured to mimic operation of a lung, wherein lung epithelium cells self-assemble on one surface of the culturing membrane and lung capillary endothelium cells self-assemble on the opposite face of the same culturing membrane. The device thus allows simulation of the structure and function of a functional alveolar-capillary unit that can be exposed to physiological mechanical strain to simulate breathing or to both air-borne and blood-borne chemical, molecular, particulate and cellular stimuli to investigate the exchange of chemicals, molecules, and cells across this tissue-tissue interface through the pores of the membrane. The device may impact the development of in-vitro lung models that mimic organ-level responses, which can be analyzed under physiological and pathological conditions.

Embodiments of the device according to the invention can be applied in numerous fields including basic biological science, life science research, drug discovery and development, drug safety testing, toxicology, chemical and biological assays, as well as tissue and organ engineering. In an embodiment, the device is a bioartificial organ device which can be used as organ-specific disease biology. Furthermore, the device can find application in organ assist devices for liver, kidney, lung, intestine, bone marrow, and other organs and tissues, as well as in organ replacement structures.

Applications of the device according to the invention may also include, but are not limited to, identification of markers of disease; assessing efficacy of anti-cancer therapeutics; testing gene therapy vectors; drug development; screening; studies of cells, especially stem cells and bone marrow cells; studies on biotransformation, absorption, clearance, metabolism, and activation of xenobiotics; studies on bioavailability and transport of chemical or biological agents across epithelial or endothelial layers; studies on transport of biological or chemical agents across the blood-brain barrier; studies on transport of biological or chemical agents across the intestinal epithelial barrier; studies on acute basal toxicity of chemical agents; studies on acute local or acute organ-specific toxicity of chemical agents; studies on chronic basal toxicity of chemical agents; studies on chronic local or chronic organ-specific toxicity of chemical agents; inhalation toxicity studies; repeated dose toxicity studies; long-term toxicity studies; chronic toxicity studies; studies on teratogenicity of chemical agents; studies on genotoxicity, carcinogenicity, and mutagenicity of chemical agents; detection of infectious biological agents and biological weapons; detection of harmful chemical agents and chemical capons; studies on infectious diseases; studies on the efficacy of chemical or biological agents to treat disease; studies on the optimal dose range of agents to treat disease; prediction of the response of organs in-vivo to biological agents; prediction of the pharmacokinetics of chemical or biological agents; prediction of the pharmacodynamics of chemical or biological agents studies concerning the impact of genetic content on response to agents; studies on gene transcription in response to chemical or biological agents; studies on protein expression in response to chemical or biological agents; and studies on changes in metabolism in response to chemical or biological agents.

The device according to the invention can also be used to screen the cells for an effect of the cells on the materials (for example, in a manner equivalent to tissue metabolism of a drug). It may be used by one to simulate the mechanical load environment of walking, running, breathing, peristalsis, flow of urine, or the beat of a heart, to cells cultured from mechanically active tissues, such as heart, lung, skeletal muscle, bone, ligament, tendon, cartilage, smooth muscle cells, intestine, kidney, skin, endothelial cells and cells from other tissues. Rather than test the biological or biochemical responses of a cell in a static environment, the investigator can apply a range of frequencies, amplitudes and duration of mechanical stresses, including tension, compression and shear, to cultured cells.

The device according to the invention can further be used for studying biotransformation, absorption, clearance, metabolism, and activation of xenobiotics, as well as drug delivery. The bioavailability and transport of chemical and biological agents across epithelial layers as in the intestine, endothelial layers as in blood vessels, and across the blood-brain barrier can also be studied. The acute basal toxicity, acute local toxicity or acute organ-specific toxicity, teratogenicity, genotoxicity, carcinogenicity, and mutagenicity, of chemical agents can also be studied. Effects of infectious biological agents, biological weapons, harmful chemical agents and chemical weapons can also be detected and studied. Infectious diseases and the efficacy of chemical and biological agents to treat these diseases, as well as optimal dosage ranges for these agents can be studied. The response of organs in-vivo to chemical and biological agents, and the pharmacokinetics and pharmacodynamics of these agents can be detected and studied using the device according to the invention. The impact of genetic content on response to the agents can be studied. The amount of protein and gene expression in response to chemical or biological agents can be determined. Changes in metabolism in response to chemical or biological agents can be studied as well using the present device.

In specific applications, the device according to the invention can particularly be advantageous. For example, some of the advantages of the device, as opposed to conventional cell cultures or tissue cultures, can for instance include, when cells are placed in the device, fibroblast, SMC (smooth muscle cell) and EC (endothelial cell) differentiation can occur that re-establishes a defined three-dimensional architectural tissue-tissue relationships that are close to the in-vivo situation, and cell functions and responses to pharmacological agents or active substances or products can be investigated at the tissue and organ levels. In addition, many cellular or tissue activities are amenable to detection in the device, including, but not limited to diffusion rate of the drugs into and through the layered tissues in transported flow channel; cell morphology, differentiation and secretion changes at different layers; cell locomotion, growth, apoptosis and the like. Further, the effect of various drugs on different types of cells located at different layers of the system may be assessed easily.

The device according to the invention can be employed in engineering a variety of tissues including, but not limited to the cardiovascular system, lung, intestine, kidney, brain, bone marrow, bones, teeth, and skin. If the device is fabricated with a suitable biocompatible and/or biodegradable material, such as poly-lactide-co-glycolide acid (PLGA), it may be used for transplantation or implantation in-vivo. Moreover, the ability to spatially localize and control interactions of several cell types presents an opportunity to engineer hierarchically, and to create more physiologically correct tissue and organ analogs. The arrangement of multiple cell types in defined arrangement has beneficial effects on cell differentiation, maintenance and functional longevity.

For drug discovery, for example, there can be two advantages for using the device according to the invention: (1) the device may be better able to mimic in-vivo layered architecture of tissues and therefore allows one to study drug effect at the organ level in addition to the cellular and tissue levels; and 2) the device may decrease the use of in-vivo tissue models and the use of animals for drug selection and toxicology studies.

In addition to drug discovery and development, the device according to the invention may be also useful in basic and clinical research. For example, it can be used to research the mechanism of tumorigenesis. It is well established that in-vivo cancer progression is modulated by the host and the tumor micro-environment, including the stromal cells and extracellular matrix (ECM). For example, stromal cells were found being able to convert benign epithelial cells to malignant cells, thus ECM was found to affect the tumor formation. There is growing evidence that cells growing in defined architecture are more resistant to cytotoxic agents than cells in mono layers. Therefore, the device may be a better means for simulating the original growth characteristics of cancer cells and thus better reflects the real drug's sensitivity of in-vivo tumors.

The device according to the invention can also allow different growth factors, chemicals, gases and nutrients to be added to different cell types according to the needs of cells and their existence in-vivo. Controlling the location of those factors or proteins may direct the process of specific cell remodelling and functioning, and may also provide the molecular cues to the whole system, resulting in such beneficial developments as neotissue, cell remodelling, enhanced secretion, and the like.

In yet another aspect, the device according to the invention can be utilized as multi cell type cellular microarrays, such as microfluidic devices. Using the device, pattern integrity of cellular arrays can be maintained. These cellular microarrays may constitute the future "lab-on-a-chip", particularly when multiplexed and automated. These miniaturized multi cell type cultures will facilitate the observation of cell dynamics with faster, less noisy assays, having built-in complexity that will allow cells to exhibit in-vivo-like responses to the array.

In yet another aspect, the device according to the invention can be utilized as biological sensors. Cell-based biosensors can provide more information than other biosensors because cells often have multifaceted physiological responses to stimuli, as well as novel mechanisms to amplify these responses. All cell types in the device can be used to monitor different aspects of an analyte at the same time; different cell type in the device can be used to monitor different analytes at the same time; or a mixture of both types of monitoring. Cells ranging from *E. coli* to cells of mammalian lines have been used as sensors for applications in environmental monitoring, toxin detection, and physiological monitoring.

In yet another aspect, the device according to the invention can be used in understanding fundamental processes in cell biology and cell-ECM interactions. The in-vivo remodelling process is a complicated, dynamic, reciprocal process between cells and ECMs. The device can be able to capture the complexity of these biological systems, rendering these systems amenable to investigation and beneficial manipulation. Furthermore, coupled with imaging tools, such as fluorescence microscopy, microfluorimetry or optical coherence tomography (OCT), trans-epithelial electrical resistance (TEER), real-time analysis of cellular behaviour in the multilayered tissues is expected using the device. Examples of cell and tissue studies amenable to real-time analysis include cell secretion and signalling, cell-cell interactions, tissue-tissue interactions, dynamic engineered tissue construction and monitoring, structure-function investigations in tissue engineering, and the process of cell remodelling matrices in-vitro.

Another example of the use of the device according to the invention is to induce tissue-tissue interfaces and complex organ structures to form within the device by implanting the device in-vivo within the body of a living animal, and allowing cells and tissues to impregnate the device and establish normal tissue-tissue interfaces. Then the whole device and contained cells and tissues is surgically removed, while perfusing the device through one or more of the fluid channels with medium and gases necessary for cell survival. This complex embodiment of the device may then be maintained viable in-vitro through continuous perfusion and used to study highly complex cell and tissue functions in their normal 3D context with a level of complexity not possible using any existing in-vitro model system.

In particular, a microchannel embodiment of the device according to the invention may be implanted subcutaneously in-vivo into an animal in which the device contains bone-inducing materials, such as demineralized bone powder or bone morphogenic proteins (BMPs), in a channel that has one or more corresponding ports open to the surrounding tissue space. A second channel can be closed during implantation by closing its end ports or filling it with a solid removable material, such as a solid rod. As a result of wound healing, connective tissues containing microcapillaries and mesenchymal stem cells would grow into the open channel of the device and, due to the presence of the bone-inducing material, will form bone with spaces that recruit circulating hematopoietic precursor cells to form fully functional bone marrow, as shown in past studies. Once this process is complete, the surgical site would be reopened and the second channel would be reopened by removing the rod or plugs and would then be connected with catheters linked to a fluid reservoir so that culture medium containing nutrients and gases necessary for cell survival could be pumped through the second channel and passed through the pores of the culturing membrane into the first channel containing die formed bone marrow. The entire microchannel device could then be cut free from the surrounding tissue, and with the medium flowing continuously into the device, would be removed from the animal and passed to a tissue culture incubator and maintained in culture with continuous fluid flow through the second channel, and additional flow can be added to the first channel as well, if desired, by connecting to their inlet and outlet ports. The microchannel device would then be used to study intact bone marrow function in-vitro as in a controlled environment.

Both biocompatible and biodegradable materials can be used in the device according to the invention to facilitate in-vivo implantation. One can also use biocompatible and biodegradable coatings. For example, one can use ceramic coatings on a metallic substrate. But, any type of coating material can be used and the coating can be made of different types of materials: metals, ceramics, polymers, hydrogels or a combination of any of these materials. Biocompatible materials include, but are not limited to an oxide, a phosphate, a carbonate, a nitride or a carbonitride. Among the oxide, the following ones are possible examples: tantalum oxide, aluminum oxide, iridium oxide, zirconium oxide or titanium oxide. In some cases, the coating can also be made of a biodegradable material that will dissolve over time and may be replaced by the living tissue. Substrates are made of materials such as metals, ceramics, polymers or a combination of any of these, and metals such as stainless steel, nitinol, titanium, titanium alloys, or aluminum and ceramics such as zirconia, alumina, or calcium phosphate are of particular interest.

The biocompatible material from which the device can be made can also be biodegradable in that it will dissolve over time and may be replaced by the living tissue. Such biodegradable materials include, but are not limited to polylactic acid-co-glycolic acid), polylactic acid, polyglycolic acid (PGA), collagen or other ECM molecules, other connective tissue proteins, magnesium alloys, polycaprolactone, hyaluric acid, adhesive proteins, biodegradable polymers, synthetic, biocompatible and biodegradable material, such as biopolymers, bioglasses, bioceramics, calcium sulfate, calcium phosphate such as, for example, monocalcium phosphate monohydrate, monocalcium phosphate anhydrous, dicalcium phosphate dehydrate, dicalcium phosphate anhydrous, tetracalcium phosphate, calcium orthophosphate phosphate, calcium pyrophosphate, alpha-tricalcium phosphate, beta-tricalcium phosphate, apatite such as hydroxyapatite, or polymers, such as for example, poly(alpha-hydroxy esters), poly(ortho ester), poly(ether esters), polyanhydrides, poly(phosphazenes), poly(propylene fumarates), poly(ester amides), poly(ethylene fumarates), poly(amino acids), polysaccharides, polypeptides, poly(hydroxy butyrates), poly(hydroxy valerates), polyurethanes, poly(malic acid), polylactides, polyglycolides, polycaprolactones, poly(glycolide-co-trimethylene carbonates), polydioxanones, or copolymers, terpolymers thereof or blends of those polymers, or a combination of biocompatible and biodegradable materials. One can also use biodegradable glass and bioactive glass self-reinforced and ultrahigh strength bioabsorbable composites assembled from partially crystalline bio absorbable polymers, like polyglycolides, polylactides and/or glycolide/lactide copolymers.

These materials may have comparably high initial strength, appropriate modulus and strength retention time from 4 weeks up to 1 year in-vivo, depending on the implant geometry. Reinforcing elements such as fibers of crystalline polymers, fibers of carbon in polymeric resins, and particulate fillers, e.g., hydroxyapatite, may also be used to provide the dimensional stability and mechanical properties of biodegradable devices. The use of interpenetrating networks (IPN) in biodegradable material construction has been demonstrated as a means to improve mechanical strength. To further improve the mechanical properties of IPN-reinforced biodegradable materials, the present device may be prepared as semi-interpenetrating networks (SIPN) of crosslinked polypropylene fumarate within a host matrix of poly(lactideco-glycolide) 85:15 (PLGA) or poly(l-lactide-co-d,l-lactide) 70:30 (PLA) using different crosslinking agents. One can also use natural poly(hydroxybutyrate-co-9% hydroxyvalerate) copolyester membranes. A skilled artisan will be able to also select other biodegradable materials suitable for any specific purposes and cell and tissue types according to the applications in which the device is used.

Preferably, a volume of the at least one limitation cavity of the at least one actuation chamber is adjusted to correspond to a predefined deflection of the culturing membrane into or from the at least one culturing chamber. Thus, the volume can particularly be arranged such that the predefined deflection corresponds to a maximum deflection of the culturing membrane. For example, the volume of the maximum deflected culturing membrane can be identical to the volume of the actuation cavity. Like this, the deflection of the culturing membrane can be conveniently limited, independently from the type and material of the culturing membrane.

In use of the device, the culturing chamber can be fully or partially filled, with medium or fluid being little compressible, compared to the media or fluids arranged in the access chamber and/or in the actuation chamber. In particular, the medium arranged in the culturing chamber can be essentially incompressible compared to the media arranged in the access chamber and/or in the actuation chamber. For example, the medium arranged in the culturing chamber can be water or a water based solution or the like and the media arranged in the access chamber and/or in the actuation chamber can be air or an air-like gas.

In another embodiment, the actuation chamber can be provided with a mixture of at least two media, wherein one medium is little or essentially not compressible compared to the media arranged in the access chamber and/or in the actuation chamber, and the other medium is compressible compared to the media arranged in the access chamber and/or in the actuation chamber. In such an embodiment, in which the volume of the limitation cavity is larger than the volume enclosed by the maximum deflected culturing membrane, the deflection of the culturing membrane can be damped rather than being immediately stopped, which can allow for a comparably gentle deflection.

Preferably, the at least one limitation cavity of the at least one actuation chamber is arranged adjacent to the at least one culturing chamber. In this context, the term "adjacent" relates to being located on the opposite side of the actuation membrane. Thus, the limitation cavity can be congruent to the culturing chamber or can partially cover the culturing chamber. Like this, a compact efficient arrangement of the device can be achieved.

The at least one actuation chamber preferably is connected to a deflection actuation channel. It can be further connected to a deflection actuation port being connected to a pressure application means for adjusting the pressure inside the at least one limitation cavity of the at least one actuation chamber. The pressure application means can be a pump or the like. In particular, the at least one actuation channel can connect the deflection actuation port and the actuation chamber. Such an arrangement of the actuation channel allows for efficiently providing a pressure regulating medium into and out of the actuation chamber. Thus, the actuation channel can particularly be a microchannel Like this, the pressure inside the actuation chamber can efficiently be adjusted, varied and controlled. With an arrangement of the deflection actuation port combined with the pressure application means, a comparably simple and efficient implementation of the actuation system can be achieved. Thus, the device preferably further includes a pressure sensor sensing a pressure inside the at least one actuation chamber. Such a pressure sensor allows for efficiently monitoring and controlling the pressure inside the actuation chamber and thus also the deflection of the culturing membrane.

Preferably, the device includes a perfusion channel having an inlet, an outlet and the at least one culturing chamber, wherein the inlet, the at least one culturing chamber and the outlet are connected. Thus, the perfusion channel can particularly be a microchannel. With such a fluidic system, cells and nutrients can efficiently be provided to the culturing membrane, such that growth of cells on the culturing membrane can be achieved and supported. Thus, the device preferably further includes at least two valves for closing the perfusion channel, wherein one of the at least two valves or microvalves is arranged between the inlet of the perfusion channel and the culturing chamber of the perfusion channel, and the other one of the at least two valves or microvalves is arranged between the culturing chamber of the perfusion channel and the outlet of the perfusion channel With such two valves, the culturing chamber can be isolated from the inlet and the outlet such that no fluid arranged in the culturing chamber can escape. In other embodiments not having a separated outlet, one single valve can be sufficient for such isolation of the culturing chamber. In particular, such isolation of the culturing chamber allows for an efficient transfer of the pressure from the actuation membrane to the culturing membrane. Or in other words, it can be prevented that deflection of the actuation membrane causes a medium in the culturing chamber to flow rather than changing its pressure for deflecting the culturing membrane. The at least two valves can be active valves or passive valves.

Thus, each of the at least two valves preferably includes a valve actuation channel, a valve port and a valve membrane dividing the valve channel from the perfusion channel Such an implementation of the valves allows for a comparable simple implementation of precisely adjustable valve actuation. In particular, control of the valves can be performed by the same or similar means as the deflection of the actuation membrane. Thus, the valve membranes of the at least two valves are sections of the actuation membrane, which allows for a comparably compact implementation of the device at a comparably low number of parts. Further, the valve ports of the at least two valves preferably are connected to pressure application means for adjusting the pressure inside the valve actuation channels of the at least two valves. Also, the device preferably further includes at least two valve pressure sensors sensing pressures inside the valve actuation channels of the at least two valves. With such pressure sensors, the pressure in the valves can efficiently be controlled and adjusted.

Preferably, the culturing membrane is sandwiched between the first body portion and the second body portion, and the actuation membrane is sandwiched between the second body portion and the third body portion. The term "to sandwich" in this context relates to clamping between different portions of the device. In particular, the term can relate to clamping the membranes directly between the plate-like first, second and third body portions. Like this, a comparably simple, compact and efficient implementation of the device can be achieved. Alternatively or additionally, the culturing membrane can be glued, plasma bonded or otherwise fixed in the device.

Preferably, the culturing membrane is at least partially plasma treated or coated with cell adhesion molecules. Such plasma treatment can be an oxygen or nitrogen plasma exposure. Such cell adhesion molecules can be fibronectin, collagen, laminin or a mixture thereof. The cellular adhesion can also be enhanced by surface functionalization of the membrane with functional molecules. The coating with cell adhesion molecules or membrane functionalization can at least be present in sections of the culturing membrane limiting the culturing chamber. Such a culturing membrane allows for efficient growing of cells on the membrane such that tissue can be modelled.

Preferably, each of the first body portion, the second body portion and the third body portion is a microplate made of a biocompatible material such as, e.g., described below. Thus, the at least one access chamber preferably is formed by a through-hole in the first body portion limited by the culturing membrane. This allows for a comparably simple efficient implementation of the access chamber(s). Also, the at least one culturing chamber preferably is formed by a through-hole in the second body portion. The through-hole forming the culturing chamber preferably has conical shape, wherein it may widen into the direction of the third body portion. This allows for a comparably simple efficient implementation of the culturing chamber(s).

Preferably, the device includes a medium source connected to the at least one culturing chamber, a medium sink connected to the at least one culturing chamber and a charging structure adapted to provide a medium from the medium source to the medium sink via the at least one culturing chamber. Thus, the medium source can be identical to the medium sink, i.e., the medium source and the medium sink can be one single physical entity. Like this, the perfusion system could also be arranged so that the culturing chamber and the charging structure would be implemented in a recirculation microfluidic system. The charging structure can be a medium pump or the like. Such an arrangement allows for an efficient implementation of a perfusion system for growing cells on the culturing membrane. For the same purpose, the device can additionally or alternatively include a cell injector for providing cells into the at least one culturing chamber. The cells can, e.g., be provided into the at least one access chamber via the through-hole and/or the perfusion channel.

Preferably, the device includes a control unit adapted to adjust and monitor operation properties of the device. Thus, the control unit preferably is adapted to control a medium flow through the at least one culturing chamber. The control unit preferably is further adapted to control cell injection into the at least one culturing chamber, for instance by controlling the concentration of the cells loaded on the membrane or the density of the adherent or confluent cells cultured on the membrane. Also, the control unit preferably is adapted to control a pressure inside the at least one actuation chamber. The control unit can also control the pressure in the valve(s) that isolate the culturing chamber. Such a control unit allows for efficiently operating the device. It can be particularly implemented as or including a computer.

These and other aspects of the invention will be apparent from and elucidated with reference to the embodiment(s) described hereinafter. Those of ordinary skill in the art will realize that the preceding and following description is illustrative only and is not intended to be in any way limiting.

BRIEF DESCRIPTION OF THE DRAWINGS

The device according to the invention is described in more detail herein below by way of exemplary embodiments and with reference to the attached drawings, in which:

FIG. 2B shows an exploded perspective view of the bioartificial organ device of FIG. 2A;

FIG. 2C shows a top view on the bioartificial organ device of FIG. 2A;

FIG. 2D shows a cross sectional view along the line A-A of the top view of FIG. 2C;

DETAILED DESCRIPTION

In the following description, certain terms are used for reasons of convenience and are not to be interpreted as limiting. The terms "right", "left", "up", "down", "under" and "above" refer to directions in the figures. The terminology includes the explicitly mentioned terms as well as their derivations and terms with a similar meaning.

Figure 1:
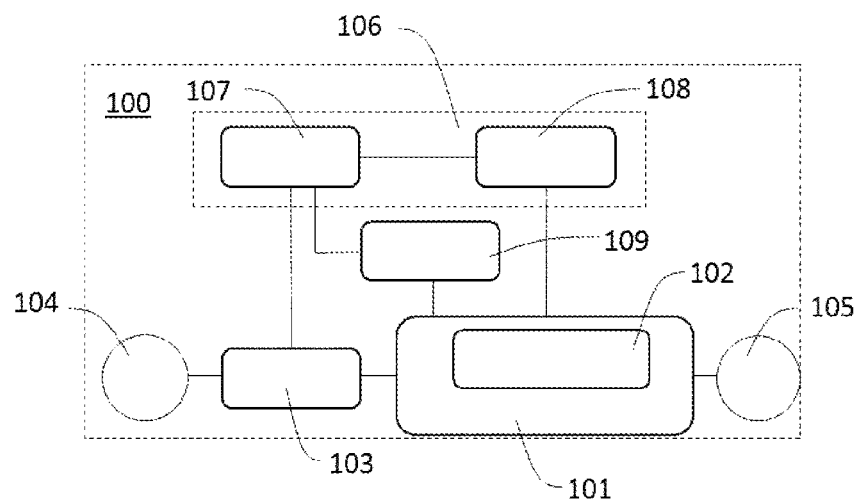
FIG. 1 shows a block diagram of a system for in-vitro modelling in-vivo tissues of organs which includes a bioartificial organ device of a first embodiment according to the invention.

FIG. 1 shows a system 100 for in-vitro modelling in-vivo tissues of organs as a first embodiment of a device according to the invention. The system 100 has a bioartificial organ device 101 with a culturing membrane as an in-vitro-barrier 102. It further includes a setup 106 having one or more CPUs 107 of a control unit connected to one or more pressure sources 108, a cell injector 109 and one or more pumps 103. The one or more pressure sources 108 and the cell injector 109 are controlled by the one or more CPUs 107 and are connected to the bioartificial organ device 101. The one or more pumps 103 are arranged in between a source reservoir 104 as medium source and the bioartificial organ device 101, which is also connected to a collecting reservoir 105 as medium sink. By means of the one or more pumps 103 and the one or more CPUs 107 a fluid flow from the source reservoir 104 to the collecting reservoir 105 via the bioartificial organ device 101 can be controlled. Although only one bioartificial organ device 101 is illustrated and described in the system, it is contemplated that a plurality of in-vitro barriers 102 may be tested and analysed within the system 100.

As will be discussed in more detail below, the bioartificial organ device 101 includes two or more ports, which place microchannels of the bioartificial organ device 101 in communication with external components of the system 100, such as the fluid reservoirs 104, 105 and the pressure sources 108. In particular, the bioartificial organ device 101 is coupled to the source reservoir 104, which may contain air, blood, water, cells, compounds, particulates and/or any other media which are to be delivered to the bioartificial organ device 101. The source reservoir 104 provides a fluid to one or more microchannels of the bioartificial organ device 101 and the collecting reservoir 105 receives fluid exiting the bioartificial organ device 101. In an alternative embodiment, the source reservoir 104, as medium source and sink, provides the fluid to the bioartificial organ device 101 and also receives the fluid which exits the bio artificial organ device 101. Thus, it is possible that separate fluid sources provide fluids to the bioartificial organ device 101 and/or separate fluid collectors accumulate the fluids exiting the bioartificial organ device 101.

In an embodiment, fluid exiting the bioartificial organ device 101 may be reused and reintroduced into the same or different input port through which it previously entered. For example, the bioartificial organ device 101 may be set up such that fluid passed through a particular central microchannel is recirculated back to the bioartificial organ device 101 and is again run through the same central microchannel. This could be used, for instance, to increase the concentration of an analyte in the fluid as it is recirculated in the bioartificial organ device 101. In another example, the bioartificial organ device 101 may be set up such that fluid is passed through the bioartificial organ device 101 and is recirculated back into the bio artificial organ device 101 and then subsequently run through another central microchannel. This could be used to change the concentration or make up of the fluid as it is circulated through another microchannel.

The one or more pumps 103 are preferably utilized to pump the fluid into the bioartificial organ device 101, although pumps in general are optional to the system 100. Fluid pumps are well known in the art and are not discussed in detail herein. As will be discussed in more detail below, each microchannel portion is preferably in communication with its respective inlet and/or outlet port, wherein each microchannel portion allows fluid to flow there through.

Each microchannel in the bioartificial organ device 101 preferably has dedicated inlet and outlet ports which are connected to respective dedicated fluid sources and/or fluid collectors to allow the flow rates, flow contents, pressures, temperatures and other characteristics of the media to be independently controlled through each central microchannel. Thus, one can also monitor the effects of various stimuli to each of the cell or tissue layers separately by sampling the separate fluid channels for the desired cellular marker, such as changes in gene expression at RNA or protein level.

The cell injector 109 is in communication with the bioartificial organ device 101, wherein the cell injector 109 is configured to inject, remove and/or manipulate cells, such as but not limited to epithelial and endothelial cells, on one or more surfaces of the interface membrane or in-vitro barrier 102 within the bioartificial organ device 101, independently of cells introduced into the bioartificial organ device 101 via the inlet ports or directly via in-vitro barrier access holes. For example, blood containing magnetic particles which pull pathogenic cells may be cultured in a separate device, wherein the mixture can be later introduced into the system 100 via the cell injector 109 at a desired time though the source reservoir 104 or directly on the in-vitro barrier 102. In an embodiment, the cell injector 109 is independently controlled, although it may be controlled by the CPUs 107. The cell injector 109 is an optional component.

Although not required in all embodiments, pressure may be applied from the one or more pressure sources 108 to create a pressure differential that causes mechanical movements within the bioartificial organ device 101. In an embodiment in which pressures are used within the bioartificial organ device 101, the pressure source 108 is controlled by the CPUs 107 to apply a pressure differential within the bioartificial organ device 101 that effectively causes one or more membranes or in-vitro barrier 102 (see below) within the bioartificial organ device 101 to expand and/or contract in response to the applied pressure differential. In an embodiment, the pressure applied to the bioartificial organ device 101 by the pressure source 108 is a positive pressure, depending on the configuration or application of the bio artificial organ device 101. Additionally or alternatively, the pressure applied by the pressure source 108 is a negative pressure, such as vacuum or suction force, depending on the configuration or application of the device 101. The pressure source 108 is preferably controlled by the CPUs 107 to apply pressure at set timed intervals or frequencies to the bioartificial organ device 101, wherein the timing intervals may be set to be uniform or non-uniform. The pressure source 108 may be controlled to apply uniform pressure in the timing intervals or may apply different pressures at different intervals. For instance, the pressure applied by the pressure source 108 may have a large magnitude and/or be set at a desired frequency to mimic a person running or undergoing exertion. The pressure source 108 may also apply slow irregular patterns, such as simulating a person sleeping. In an embodiment, the CPUs 107 operate the pressure source 108 to randomly vary intervals of applying pressure to cause cyclic stretching patterns that simulate irregularity in breath rate and tidal volumes during natural breathing.

One or more sensors may be coupled to the bioartificial organ device 101 to monitor one or more areas within the bioartificial organ device 101, wherein the sensors provide monitoring data to the CPUs 107. One type of sensor is preferably a pressure sensor which provides data regarding the amount of pressure in one or more operating or central microchannels of the bioartificial organ device 101. Pressure data from opposing sides of the microchannel walls may be used to calculate real-time pressure differential information between the operating and central microchannels. The monitoring data would be used by the CPUs 107 to provide information on the device's operational conditions as well as how the cells are behaving within the bioartificial organ device 101, in particular environments in real time. The sensor may be an electrode, have infrared, optical such as, e.g., a camera or LED, or magnetic capabilities or utilize any other appropriate type of technology to provide the monitoring data. For instance, the sensor may be one or more microelectrodes which analyse electrical characteristics across the culturing membrane or in-vitro barrier 102, such as, e.g., potential difference, resistance, and short circuit current, to confirm the formation of an organized barrier, as well as its fluid/ion transport function across the culturing membrane or in-vitro barrier 102. It should be noted that the sensor may be external to the bioartificial organ device 101 or be integrated within the bioartificial organ device 101. It is contemplated that the CPUs 107 control operation of the sensor, although it is not necessary.

The following applies to the rest of this description. If, in order to clarify the drawings, a figure contains reference signs which are not explained in the directly associated part of the description, then the reference signs refer to previous description sections.

Figure 2A:
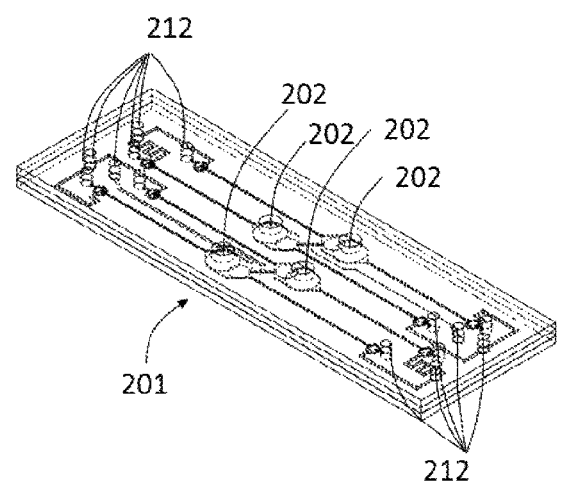
FIG. 2A shows a perspective view of a bioartificial organ device of a second embodiment of a device according to the invention.

FIGS. 2A and 2B illustrate a perspective view of a bioartificial organ device 201 of a second embodiment of a device according to the invention, in an assembled view and in an exploded view, respectively. The bioartificial organ device 201 is equipped with four in-vitro barriers 202 and includes a plurality of ports 212 that will be described in more detail below. The bioartificial organ device 201 is composed of different body portions, including a bottom body 203 as third body portion, an actuation membrane 204, an intermediate body 205 as second body portion, a thin porous culturing membrane 206 and a top body 207 as first body portion. Each of the bottom body 203, intermediate body 205 and top body 207 has an essentially rectangular plate-like shape. Each of the actuation membrane 204 and the culturing membrane 206 has an essentially rectangular shape.

The bottom body 203 includes two deflection actuation channels 210 and four valve actuation channels 209 in which a fluid, preferably air, is arranged to control actuation of deflection of the actuation membrane 204 and of microvalves, respectively. Each of the deflection actuation channels 210 connects a deflection inlet 211 with two actuation chambers 220 each having a limitation cavity, and each of the valve actuation channels 209 connects a valve inlet 208 with two microvalve chambers 217.

The actuation membrane 204 is configured to be mounted or sandwiched between the bottom body 203 and the intermediate body 205. It contains a plurality of through-holes 214, that is, two groups of three through-holes with each group being arranged at a longitudinal end of the actuation membrane 204. Each group of the plurality of through-holes 214 has two valve inlet holes 274 at positions corresponding to the valve inlets 208 of the bottom body 203 and one actuation inlet hole 284 at positions corresponding to the deflection inlets 211 of the bottom body 203. The through-holes 214 allow the fluid to access the deflection actuation channels 210 and the valve actuation channels 209 located in the bottom body 203.

The intermediate body 205 includes four perfusion channels 215 extending longitudinally along the intermediate body 205. Further, the intermediate body 205 is equipped with valve inlet through-holes 265 at positions corresponding to the valve inlets 208 of the bottom body 203 and with actuation inlet holes 295 at positions corresponding to the deflection inlets 211 of the bottom body 203. Each of the perfusion channels 215 connects a perfusion inlet 275 with a culturing chamber 221 and a perfusion outlet 285. Each of the four culturing chambers 221 is provided as a conical through-hole in the intermediate body 205, widening into the direction of the actuation membrane 204.

The culturing membrane 206 is configured to be mounted or sandwiched between the intermediate body 205 and the top body 207. It contains a plurality of through-holes 264 at positions corresponding to the valve inlets 208 of the bottom body 203, at positions corresponding to the deflection inlets 211 of the bottom body 203, at positions corresponding to the perfusion inlets 275 of the intermediate body 205, and at positions corresponding to the perfusion outlets 285 of the intermediate body 205.

The top body 207 includes four access chambers 213 each formed by a through-hole. The access chambers 213 are located in correspondence with the location of the culturing chambers 221 of the intermediate body 205. The top body 207 further includes a plurality of port through-holes 216 comprising perfusion inlet holes 266 at positions corresponding to the valve inlets 208 of the bottom body 203, perfusion outlet holes 276 at positions corresponding to the deflection inlets 211 of the bottom body 203, valve inlet holes 286 at positions corresponding to the valve inlets 208 of the bottom body 203 and actuation inlet holes 296 at positions corresponding to the deflection inlets 211 of the bottom body 203. Furthermore, the top body 207 is equipped with four in-vitro barrier access through-holes 213 as access chambers for accessing the in-vitro barriers or culturing membrane 206.

The bottom body 203 may be made of a non-flexible material, although it is contemplated that it can be alternatively made of a flexible material. The bottom body 203, the intermediate body 205 and the top body 207 are preferably made of an essentially non-flexible biocompatible polymer, including but not limited to cyclic olefin copolymer, polystyrene or any other elastomeric or thermoplastic material or other materials like glass, silicon, soft or hard plastic, and the like. However, the bodies 203, 205 and 207 can be made of soft material as well, and can be different from each other. It is contemplated that the thin porous culturing membrane 206 can be made of a material that is different from the material of the bodies 203, 205, 207. The culturing membrane 206 is preferably made of an essentially flexible material, such as polydimethylsiloxane, or any other flexible or non-flexible material, such as polyimide, parylene, or the like. The actuation membrane 204 is preferably made of an essentially flexible material such as silicone rubber, preferably polydimethylsiloxane, or polyimide, parylene or any other flexible material.

In operation, the valve actuation channels 209 and the deflection actuation channels 210 of the bottom body 203 are filled with a fluid, preferably air, to control deflection of the actuation membrane 204 and closing of the microvalves. Thus, the fluid is provided to the valve actuation channels 209 via valve ports formed by the valve inlet holes 286 of the top body 207, the corresponding through-holes 264 of the culturing membrane 206, the valve inlet holes 265 of the intermediate body 205, the valve inlet holes 274 of the actuation membrane 204 and the valve inlets 208 of the bottom body 203. Further, the fluid is provided to the deflection actuation channels 210 via deflection ports formed by the actuation inlet holes 296 of the top body 207, the corresponding through-holes 264 of the culturing membrane 206, the actuation inlet holes 295 of the intermediate body 205, the actuation inlet holes 284 of the actuation membrane 204 and the deflection inlets 211 of the bottom body 203.

Also, the perfusion channels 215 of the intermediate body 205 are filled with a comparably incompressible fluid such as water or a water based solution. Thus, the comparably incompressible fluid is provided into the perfusion channels 215 via perfusion inlet ports formed by the perfusion inlet holes 266 of the top body 207, the corresponding through-holes 264 of the culturing membrane 206 and the perfusion inlets 275 of the intermediate body 205, and provided out of the perfusion channels 215 via perfusion outlet ports formed by the perfusion outlet holes 276 of the top body 207, the corresponding through-holes 264 of the culturing membrane 206 and the perfusion outlets 285 of the intermediate body 205.

FIG. 2C shows a top view of the bioartificial organ device 201 wherein some elements of the bioartificial organ device 201 which are not visible on the surface are indicated with dotted lines. Thus, it is illustrated that the sections of the culturing membrane 206 which are accessible via the access chambers 213 form the four in-vitro barriers 202. As can be seen in the cross sectional view of FIG. 2D, at each of the in-vitro barriers 202 the culturing membrane 206 separates the conical culturing chamber 221 of the intermediate body 205 from the access chamber 213 of the top body 207. The culturing chamber 221 is connected to the left-sided perfusion inlet 275 and to the right-sided perfusion outlet 285 by the perfusion channel 215. Further, close to each of the in-vitro barriers 202 an actuation valve 219 including one of the actuation chambers 220 of the bottom body 203 and its adjacent section of the actuation membrane 204 is arranged.

Figure 2E:
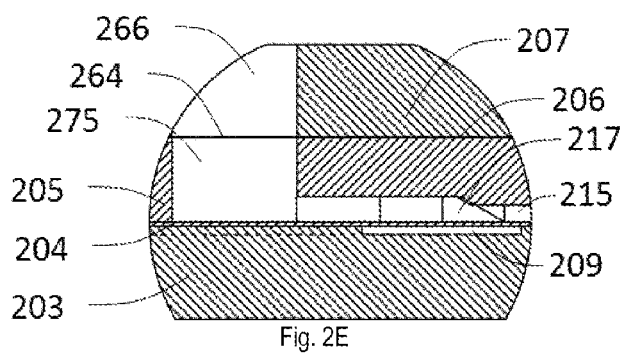
FIG. 2E shows detail B of the cross sectional view of FIG. 2D.
Figure 2F:
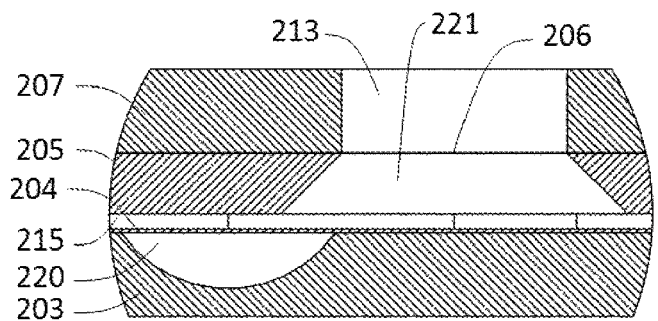
FIG. 2F shows detail C of the cross sectional view of FIG. 2D.
Figure 2G:
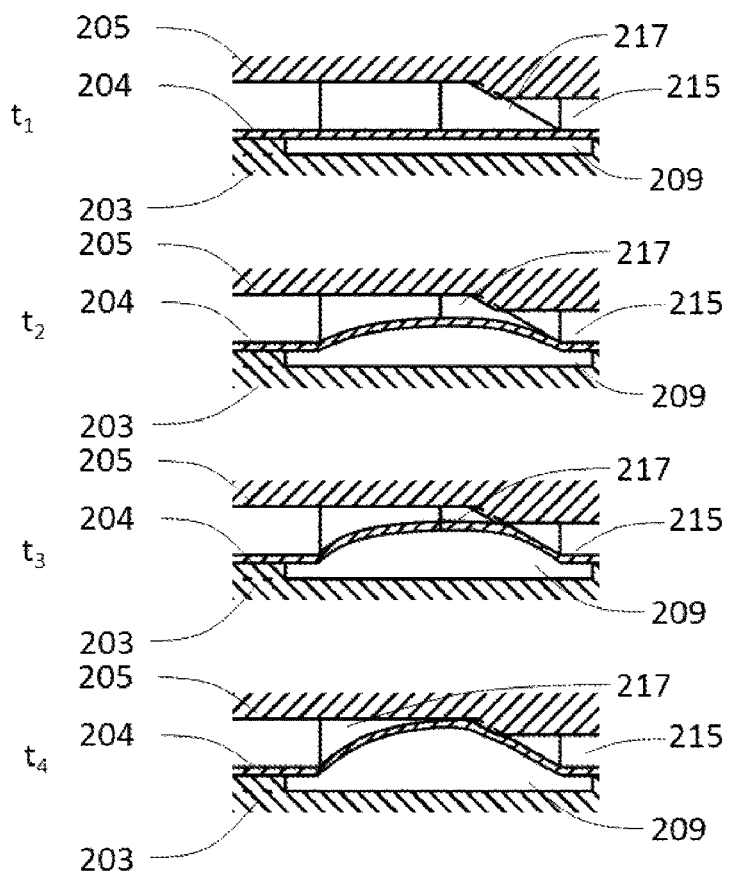
FIG. 2G shows detail B of the cross sectional view of FIG. 2D at different points in time during actuation of an actuation membrane or microvalve.
Figure 2H:
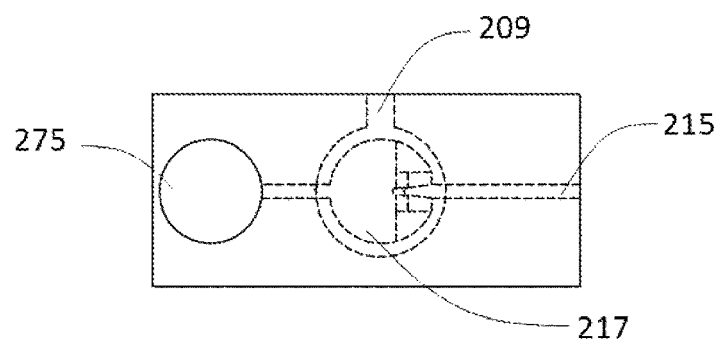
FIG. 2H shows a detailed top view of detail B of the cross sectional view of FIG. 2D.
Figure 2J:
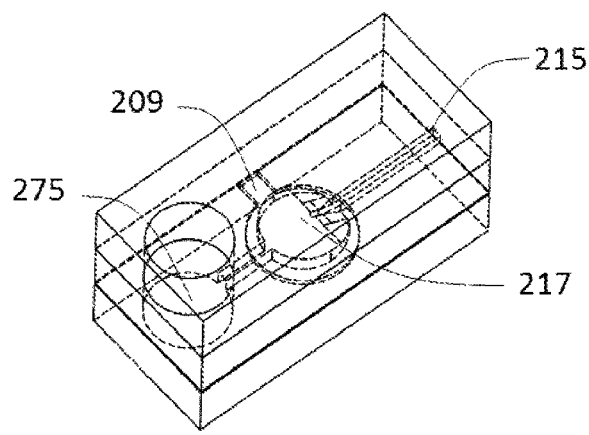
FIG. 2J shows a perspective view of detail B of the cross sectional view of FIG. 2D.

Particularly considering the detailed views of FIGS. 2E, 2H and 2J, it can be seen that in the intermediate body 205 the perfusion channel 215 passes over into the perfusion inlet 275 and the perfusion outlet 285 via microvalve chambers 217. Thus, each of the microvalve chambers 217 of the intermediate body 205 is separated from one of the valve actuation channels 209 of the bottom body 203 by the actuation membrane 204. Like this, each of the microvalve chambers 217, together with its adjacent section of the actuation membrane 204 and valve actuation channel 209, forms a microvalve.

In FIG. 2G, the microvalve described hereinbefore is shown at different points in time during actuation. Thus, at time point $t_1$, the actuation membrane 204 is not actuated and the perfusion channel 215 is in a completely open position. At time point $t_2$, the actuation membrane 204 is partly actuated and the perfusion channel 215 is partly closed to the microvalve chamber 217. At time point $t_3$, the actuation membrane 204 is increasingly actuated and the perfusion channel 215 is increasingly closed to the microvalve chamber 217 analogously with the actuation of the actuation membrane 204. At time point $t_4$, the actuation membrane 204 is completely actuated and the perfusion channel 215 is in a completely closed position.

Particularly considering the detailed view of FIG. 2F it can be seen that the culturing chamber 221 of the intermediate body 205 is upwardly separated or divided from the access chamber 213 of the top body 207 by the culturing membrane 206. Also, the culturing chamber 221 is downwardly separated from the actuation chamber 220 of the bottom body 203 by the actuation membrane 204, wherein the actuation chamber 220 or its limitation cavity is located neighbouring but off-centred to the culturing chamber 221.

When a suction force or vacuum is applied to the actuation channel 210 via one of the deflection ports including one of the deflection inlets 211, the actuation membrane 204 is negatively or downwardly deflected into the actuation chamber 220 as a result of the decrease of the pressure in the actuation chamber 220. When the actuation valves 219 are deflected, the pressure of the fluid, preferably physiological medium, blood, blood serum, oil or air, contained in the culturing chambers 221 and in the perfusion channels 215 decreases and induces a deflection of the in-vitro barrier 202 or culturing membrane 206, respectively. To avoid leakages of the fluid contained in the culturing chambers 221 and the perfusion channels 215, the microvalves are pneumatically actuated as long as the actuation valves 219 are in use. As a result, the microvalves block the perfusion channels 215 on both sides.

In an embodiment, the thin porous culturing membrane 206 is treated with an oxygen plasma, a nitrogen-rich plasma or a similar plasma favouring the adhesion of cells, or is coated with a solution containing adhesion molecules, such as fibronectin, collagen, laminin, or any other molecules, or a mixture of those molecules, favouring the adhesion of cells on the culturing membrane 206. This can be done for instance by applying such molecules via the in-vitro barrier access chamber 213 and/or via one of the perfusion ports and the perfusion channels 215. Then, cells, for instance epithelial, endothelial, fibroblasts, macrophages, dendritic cells, mesenchymal stem cells, or any other cells, are introduced in the perfusion channel 215 via one of the perfusion ports until they reach the culturing chamber 221. The bioartificial organ device 201 is then incubated and flipped by 180° to let the cells attach on the culturing membrane 206. Once the cells are adhered, the bioartificial organ device 201 is flipped again in its original position and the cells, for instance again epithelial, endothelial, fibroblasts, macrophages, dendritic cells, mesenchymal stem cells, or any other cells, are introduced on the in-vitro barriers 202 via the access chambers 213. Once the cells are attached, the cell culturing membrane 206 or the in-vitro barrier 202, respectively, can be mechanically stretched by applying a cyclic pressure at the deflection inlet 211 via the deflection port.

The three-dimensional design of the microvalve shown in detail above allows for limiting the volume of media being pushed through the perfusion channel 215 into the direction of the culturing membrane 206. Thus, the culturing membrane 206 can be precisely deflected to a predefined extent and in a predefined manner. It is one of the aims of the microvalve to level the culturing membrane 206 at any desired strain condition and at any desired time point. This allows predefining the deflection of the culturing membrane 206 and precisely controlling the desired predefined strain of the culturing membrane 206. The levelling of the culturing membrane 206 can be performed at regular or irregular time intervals, either to reset the predefined level of strain or define a new strain level. The levelling of the culturing membrane 206 might, for instance, be necessary in the case of small leakages, or evaporation through the culturing membrane 206 and/or through an in-vitro barrier. This may, for example, take place when pores of the culturing membrane 206 are comparably large and/or if the integrity of the in-vitro barrier is damaged following a mechanical, chemical or biophysical stress or a combination thereof. The need of a levelling of the culturing membrane may also take place if a portion of or all the culturing medium is partly or totally sampled for further analysis.

One or several passive or one or several active microvalves or a combination thereof can be used to level the culturing membrane 206 at any predefined strain condition. Active microvalves can either be normally closed or normally open valves.

The levelling of the culturing membrane 206 at a predefined strain level can easily be performed by creating a hydrostatic pressure difference between the perfusion inlet 275 and/or perfusion outlet 285 and/or the access chamber 213 by adding or removing cell culture medium or similar solution for cell culture. The predefined strain can also be created by applying a positive or a negative pressure either at the perfusion inlet 275 and/or perfusion outlet 285 and/or at the access chamber 213 or a combination thereof. The predefined strain can also be defined by varying the pressure in one or several actuation chambers 220. Further the levelling can be achieved by pumping cell culture medium or any fluid in or out of the culturing chamber 221, e.g., using an integrated pumping system as shown below.

In a preferred embodiment, the predefined level of strain of the culturing membrane 206 is close to zero and is achieved by a combination of hydrostatic pressure difference between the perfusion inlet 275, the perfusion outlet 285 and the access chamber 213, the residual stresses of the actuation membrane 204 and of the culturing membrane 206, and the closing of the normally closed microvalve or a combination thereof. Instead of a normally closed microvalve, a normally open microvalve could also be used.

Figure 2K:
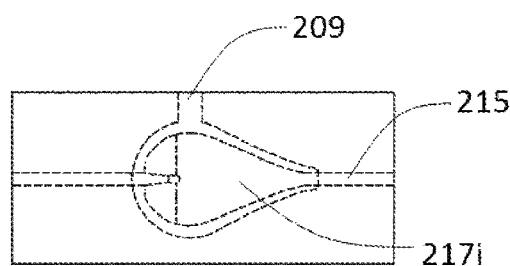
FIG. 2K shows a top view of a modified embodiment of the microvalve of FIG. 2D.

In FIG. 2K, a variation of a microvalve as alternative to the microvalve hereinbefore is shown and can be embodied in the same bioartificial organ device 201 shown hereinbefore. Compared to the microvalve described in detail hereinbefore, the microvalve of FIG. 2K has an asymmetric microvalve chamber 217i. In particular, the microvalve chamber 217i has in the top view of FIG. 2K the shape of a drop, wherein the thin end of the drop passes over into the perfusion channel 215 and the wide end of the drop is connected to the perfusion inlet 275.

Figure 2L:
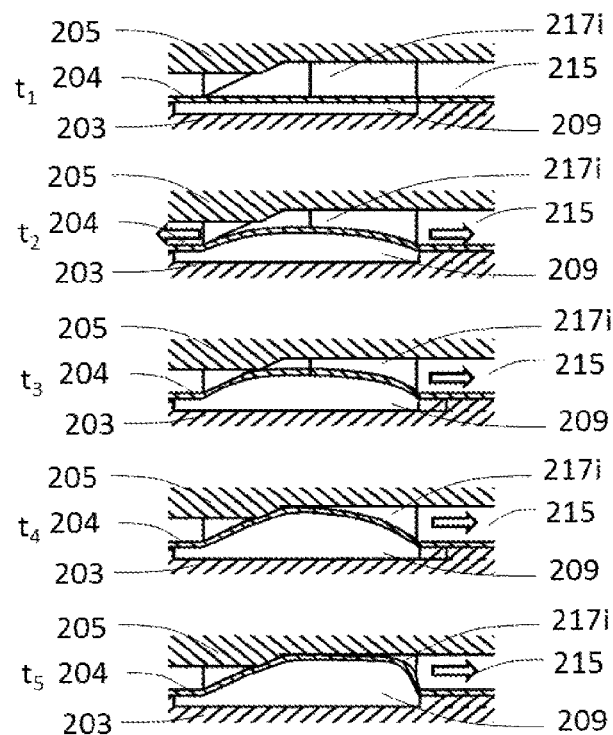
FIG. 2L shows the microvalve of FIG. 2K at different points in time during pumping.

FIG. 2L shows the microvalve with the asymmetric microvalve chamber 217i during pumping of a medium. Thus, at time point $t_1$, the actuation membrane 204 is not actuated and the perfusion channel 215 is in a completely open position. At time point $t_2$, the actuation membrane 204 is partly actuated and the medium is forwarded into the perfusion channel 215 as well as into the direction of the perfusion inlet 275. At time point $t_3$, the actuation membrane 204 is further actuated and connection to the perfusion inlet 275 is closed. At time point $t_4$, the actuation membrane 204 is increasingly actuated and the medium is forwarded into the perfusion channel 215 only. No pumping into the direction of the perfusion inlet is performed. At time point $t_5$, the actuation membrane 204 is completely actuated and final pumping of the medium into the perfusion channel 215 is effected.

Figure 2M:
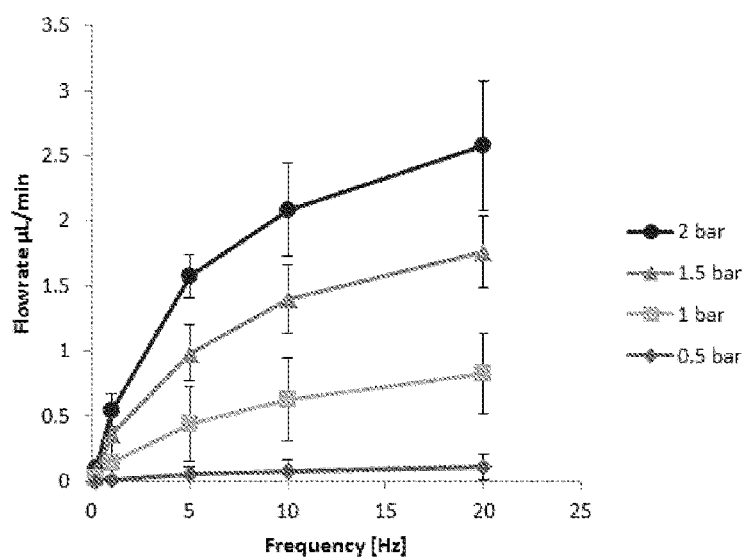
FIG. 2M shows flow rates obtained with the microvalve of FIG. 2K at various frequencies and actuation pressures.

As shown in FIG. 2M at, with each actuation (closing and/or opening) of the microvalve a flow of the solution or medium contained in the microvalve chamber 217i is forced in or out of the culturing chamber 221 via the perfusion channel 215 and in or out of the perfusion inlet 275. The flow that is forced in or out of the culturing chamber 221 should be minimized in order not to affect the predefined strain of the culturing membrane 206. One possible design of the microvalve to fulfil this objective is the minimization of the size of the microvalve cavity, minimizing the volume displaced when the microvalve closes or opens. A drawback of this solution can be the comparably high pressure required to actuate the comparably small membrane 204 and the related problems, such as the sticking of the actuation membrane 204 against the microvalve chamber 217i due to the high pressure that may need special anti-adhesion coatings. To circumvent this problem, one can reduce the cross-section of the perfusion channel 215, increasing the hydraulic resistance of the perfusion channel 215 and thus decreasing the flow rate according to Poiseuille law.

Another possibility is to design the microvalve chamber 217i so that the bidirectional flow generated by the closing of the microvalve 3002 is asymmetric, and preferably flows into the direction of the perfusion inlet 275 rather than in the perfusion channel 215 and the culturing chamber 221. This can be achieved by first closing the perfusion inlet from the microvalve chamber 217i while keeping the outlet to the perfusion channel 215 open. This is for instance performed using a three-dimensional geometry of the microvalve chamber 217*i* as explained. The three-dimensional valve has a diameter in the millimetre range that enables a rapid deflection of the actuation membrane 204. At time point $t_2$, the actuation membrane 204 meets the intermediate body 205, which has a lower protrusion, corresponding to the inlet of the perfusion channel 215. This immediately blocks the flow in direction of the culturing membrane 206. While the pressure in the actuation channel 209 continues to rise, the actuation membrane 204 is further deflected. The advantage of this system is that it does not need a large pressure, as the dimensions of the microvalve can be in the millimetre size. In addition, a tight closing of the perfusion channel can be guaranteed. Such three-dimensional microvalves can easily be produced by using 3D printing technologies as well as stereolithography, photolithography, standard milling, lamination, injection molding, hot embossing or a combination thereof.

In one embodiment, it is envisaged to use an asymmetric valve to perform the levelling of the culturing membrane 206, in order to limit the flow pushed in the perfusion channel 215 in the direction of the culturing membrane 206.

In another embodiment, it is envisaged to use the asymmetric valve as pump. In sharp contrast to existing peristaltic pumps, which mostly use three valve cavities to pump fluid, the asymmetric microvalve only needs one cavity to pump fluid. This represents a great simplification and advantage, as the set-up would be simplified with one actuation channel per pump. The flow rate of the pumped fluid can be regulated by the geometry, e.g., the size of the pump cavity, the applied actuation frequency, as well as the applied force magnitude to deflect the membrane. The membrane can be deflected, using different actuation principles e.g., magnetic, pneumatic (preferred), electric or using a shape memory alloy. The pump could be used to transport cell culture medium, growth factors, drugs, xenobiotics or other substances in the culturing chamber. It is also envisaged to create a recirculating perfusion system.

In a preferred embodiment, the asymmetric valve is made of a microvalve cavity that contains an inclined wall, upon which the actuation membrane is deflected. A small inlet of the perfusion channel is created in the inclined wall to limit the flow induced by the actuation of the microvalve to be pushed or drawn in or out of the culturing chamber 221.

Figure 3A:
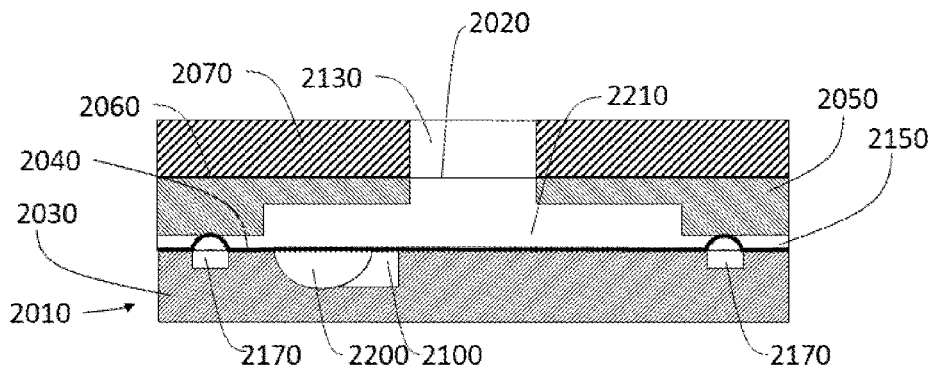
FIG. 3A shows a cross sectional view of a bioartificial organ device of a third embodiment of a device according to the invention.
Figure 3B:
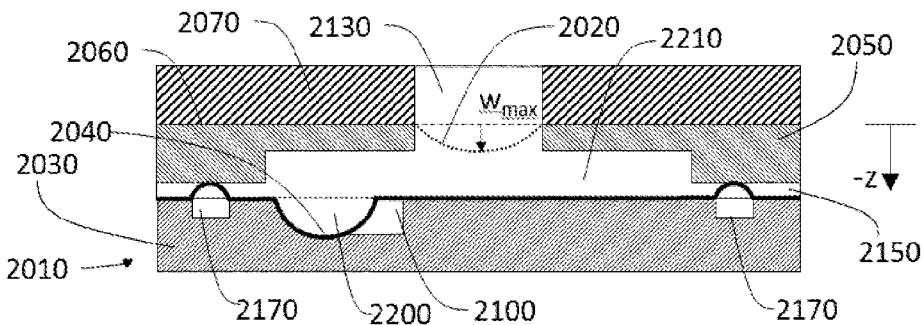
FIG. 3B shows a cross sectional view of the bioartificial organ device of FIG. 3A in deflected or actuated position.

FIGS. 3A and 3B show views of a bioartificial organ device 2010 of a third embodiment of a device according to the invention. In general, the bioartificial organ device 2010 is essentially identically embodied as the bioartificial organ device 201 described above. The bioartificial organ device 2010 includes a bottom body 2030 as a third body portion with deflection actuation channels 2100, valve actuation channels, microvalve chambers 2170 and actuation chambers 2200 having limitation cavities. On top of the bottom body 2030 an intermediate body 2050 with perfusion channels 2150 and culturing chambers 2210 is arranged as second body portion, wherein an actuation membrane 2040 is sandwiched between the bottom body 2030 and the intermediate body 2050. On top of the intermediate body 2050 a top body 2070 with access chambers 2130 is arranged as first body portion, wherein a thin porous culturing membrane 2060 is sandwiched between the intermediate body 2050 and the top body 2070. Sections of the culturing membrane 2060 being located in or below the access chambers 2130 of the top body 2070 form in-vitro barriers 2020.

FIG. 3A illustrates schematically the mechanism responsible for the mechanical stretching of the in-vitro barrier 2020. Once the fluid, preferably cell culture medium, fills the culturing chamber 2210 and a fluid, preferably air, fills the actuation channels 2100, a positive pressure is induced in the microvalve chambers 2170 via the valve actuation channels, which causes the actuation membranes 2040 to positively or upwardly deflect. Thus, the perfusion channels 2150 are closed on both sides of the culturing chambers 2210.

As shown in FIG. 3B, a negative pressure in the actuation chambers 2200 then negatively or downwardly deflects the actuation membranes 2040 into the limitation cavity of the actuation chamber 2200, which induces positive deflection of the in-vitro barrier 2020 in a z- or downward direction. In a preferred embodiment, the volume of the limitation cavity is identical to the displaced volume of the in-vitro barrier 2020, so that the maximum deflection $w_{max}$ of the in-vitro barrier 2020 is limited by the limitation cavity. The stress in the in-vitro barrier 2020 is thus very well controlled and kept constant, regardless of the mechanical properties of the actuation membrane 2040 and of the culturing membrane 2060.

Referring to FIGS. 3A and 3B, it is also contemplated to use passive microvalves, microvalves actuated by magnetic forces, or pneumatic actuated microvalves or a combination thereof, to close the perfusion channels 2150. The actuated microvalves can either be designed in a normally closed or a normally open mode. It is also contemplated to use the bioartificial organ device 2010 without microvalves, by slightly increasing the volume of the actuation chamber 2200 in order to compensate the volume of the fluid transported in the perfusion channels 2150 at each actuation cycle.

Figure 4:
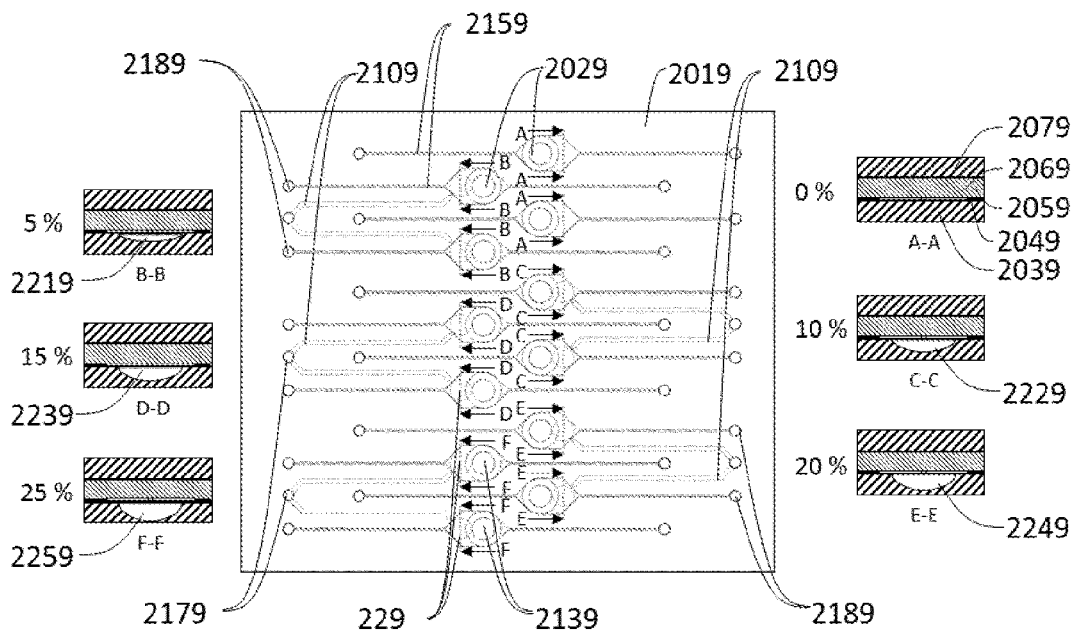
FIG. 4 shows a top view of a bioartificial organ device of a fourth embodiment of a device according to the invention.

FIG. 4 shows a bioartificial organ device 2019 of a fourth embodiment of a device according to the invention. The bioartificial organ device 2019 is principally similarly arranged as the bioartificial organ device 201 and the bioartificial organ device 2010 described above. The bioartificial organ device 2019 includes a bottom body 2039 as a third body portion with five pairs of deflection actuation channels 2109 connected to five deflection inlets 2189 on one side and to ten actuation chambers 229 on the opposite side. On top of the bottom body 2039, an intermediate body 2059 with twelve perfusion channels 2159 connected to twelve perfusion inlets 2189, twelve culturing chambers and twelve perfusion outlets 2179 is arranged as second body portion, wherein an actuation membrane 2049 is sandwiched between the bottom body 2039 and the intermediate body 2059. On top of the intermediate body 2059, a top body 2079 with twelve access chambers 2139 is arranged as first body portion, wherein a thin porous culturing membrane 2069 is sandwiched between the intermediate body 2059 and the top body 2079. Sections of the culturing membrane 2069 being located in or below the access chambers 2139 of the top body 2079 form twelve in-vitro barriers 2029.

Each of the ten actuation chambers 229 is associated to one of the twelve culturing chambers. The actuation chambers 229 have limitation cavities with varying volumes. Thus, the volumes of the different limitation cavities 2219, 2229, 2239, 2249, 2259 of the actuation chambers 229 correspond to a specific linear strain value given in percentage of the strain taking place in the in-vitro barrier 2029. Shown in cross sectional view along lines A-A are limitation cavities being zero and not inducing any strain (0% strain). The two actuation chambers 229, shown in cross sectional view along lines B-B, have limitation cavities 2219, generating 5% strain. The two actuation chambers 229, shown in cross sectional view along lines C-C, have limitation cavities 2229, generating 10% strain. The two actuation chambers 229, shown in cross sectional view along lines D-D, have limitation cavities 2239 generating 15% strain. The two actuation chambers 229, shown in cross sectional view along lines E-E, have limitation cavities 2249, generating 20% strain. The two actuation chambers 229, shown in cross sectional view along lines F-F, have limitation cavities 2259, generating 25% strain.

Thus, this possible embodiment of the bioartificial organ device 2019 allows different linear strains of the in-vitro barriers 2029 on a single bioartificial organ device 2019. It is to note that any values contained within the strains given above can be realized. The preferred strain is 10%, but can be between 0 and 30%. Positive strains are also possible as described in more detail below.

Figure 5A:
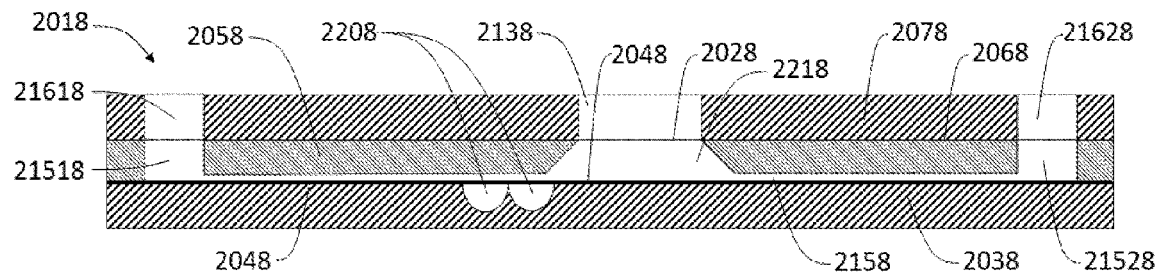
FIG. 5A shows a cross sectional view of a bioartificial organ device of a fifth embodiment of a device according to the invention having two limitation cavities per actuation chamber.

FIG. 5A shows a bioartificial organ device 2018 of a fifth embodiment of a device according to the invention. The bioartificial organ device 2018 is principally similarly arranged as the bioartificial organ device 201, the bioartificial organ device 2010 and the bioartificial organ device 2019 described above. The bioartificial organ device 2018 includes a bottom body 2038 as a third body portion, with deflection actuation channels connected to deflection inlets on one side and to actuation chambers 2208 on the opposite side. On top of the bottom body 2038, an intermediate body 2058 with perfusion channels 2158 connected to perfusion inlets 21518, culturing chambers 2218 and perfusion outlets 21528 is arranged as second body portion, wherein an actuation membrane 2048 is sandwiched between the bottom body 2038 and the intermediate body 2058. On top of the intermediate body 2058, a top body 2078 with perfusion inlet holes 21618, access chambers 2138 and perfusion outlet holes 21628 is arranged as first body portion, wherein a thin porous culturing membrane 2068 is sandwiched between the intermediate body 2058 and the top body 2078. Sections of the culturing membrane 2068 being located in or below the access chambers 2138 of the top body 2078 form in-vitro barriers 2028. Each of the actuation chambers of the bottom body 2038 of the bioartificial organ device 2018 is equipped with two limitation cavities 2208 having a rounded bottom surface. The diameter of the actuation cavities 2208 can, e.g., be between 300 micrometers and 10 millimeters, and is preferably 3.5 millimeters. The limitation cavities 2208 can, e.g., be depressurized individually, either to create 0% strain in the in-vitro barrier 2028 by not depressurizing the limitation cavities 2208, or, e.g., 5% strain in the in-vitro barrier 2028 by depressurizing one of the limitation cavities 2208 so that the actuation membrane 2048 is completely deflected in one of the limitation cavities 2208 while the other limitation cavity 2208 remains at atmospheric pressure, or 10% strain in the in-vitro barrier 2028 by depressurizing both limitation cavities 2208.

Figure 5B:
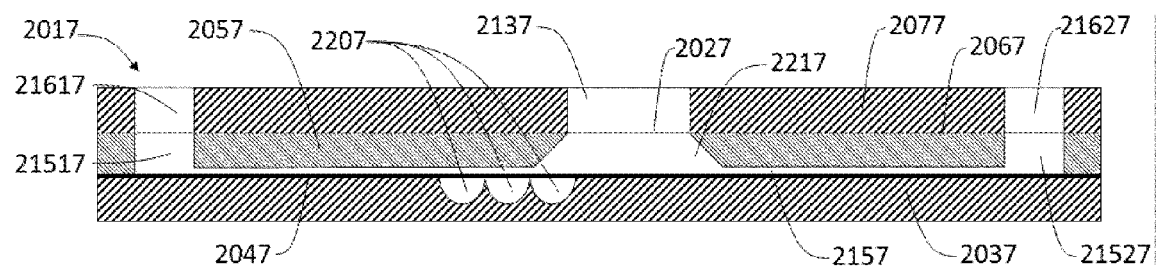
FIG. 5B shows a cross sectional view of a bioartificial organ device of a sixth embodiment of a device according to the invention having three limitation cavities per actuation chamber.

FIG. 5B shows a bioartificial organ device 2017 of a sixth embodiment of a device according to the invention. The bioartificial organ device 2017 is generally identical to the bioartificial organ device 2018 described above. The bioartificial organ device 2017 includes a bottom body 2037 as a third body portion, with deflection actuation channels connected to deflection inlets on one side and to actuation chambers 2207 on the opposite side. On top of the bottom body 2037, an intermediate body 2057 with perfusion channels 2157 connected to perfusion inlets 21517, culturing chambers 2217 and perfusion outlets 21527 is arranged as second body portion, wherein an actuation membrane 2047 is sandwiched between the bottom body 2037 and the intermediate body 2057. On top of the intermediate body 2057, a top body 2077 with perfusion inlet holes 21617, access chambers 2137 and perfusion outlet holes 21627 is arranged as first body portion, wherein a thin porous culturing membrane 2067 is sandwiched between the intermediate body 2057 and the top body 2077. Sections of the culturing membrane 2067 being located in or below the access chambers 2137 of the top body 2077 form in-vitro barriers 2027. Each of the actuation chambers of the bottom body 2037 of the bioartificial organ device is equipped with three limitation cavities 2207 having a rounded bottom surface. The diameter of the actuation cavities 2207 can, e.g., be between 300 micrometers and 10 millimeters, and is preferably 3.5 millimeters. The limitation cavities 2207 can, e.g., be depressurized individually, either to create 0% strain in the in-vitro barrier 2027 by not depressurizing the limitation cavities 2207, or, e.g., 5% strain in the in-vitro barrier 2027 by depressurizing one of the limitation cavities 2207 so that the actuation membrane 2047 is completely deflected in one of the limitation cavities 2207 while the other limitation cavities 2207 remain at atmospheric pressure, or 10% strain in the in-vitro barrier 2027 by depressurizing two limitation cavities 2207 so that the actuation membrane 2047 is completely deflected in two of the limitation cavities 2207 while the other limitation cavity 2207 remains at atmospheric pressure, or 15% strain in the in-vitro barrier 2027 by depressurizing all three limitation cavities 2207.

As it is evident to a person skilled in the art, the number of limitation cavities can be increased such that the volume of the actuation cavities can be designed and fabricated so that specific values of strains can be induced in the respective in-vitro barrier. The shape of the limitation cavities can be half-spherical with a vertical half-radius preferably being between 100 micrometers and 5 millimeters, with a preferred depth of about 549 micrometers for about 5% strain, about 668 micrometers for about 10% strain, about 753 micrometers for about 15% strain, about 823 micrometers for about 20% strain, about 884 micrometers for about 25% strain and about 939 micrometers for about 30% strain. Alternatively, the limitation cavities can be rectangular. It is contemplated that the actuation cavity can also take other shapes, such as half-circular shapes, ellipsoidal shape, quadratic shape or triangular shape.

A diameter of the in-vitro barriers of all embodiments of bioartificial organ devices described herein can be in a range of about 100 micrometers to about 10 millimeters, and is preferably between 1 and 5 millimeters. In the shown embodiments, the in-vitro barriers have circular diameters, but it is contemplated that the in-vitro barriers can have elliptical, quadratic or rectangular surfaces, or the like.

Figure 6A:
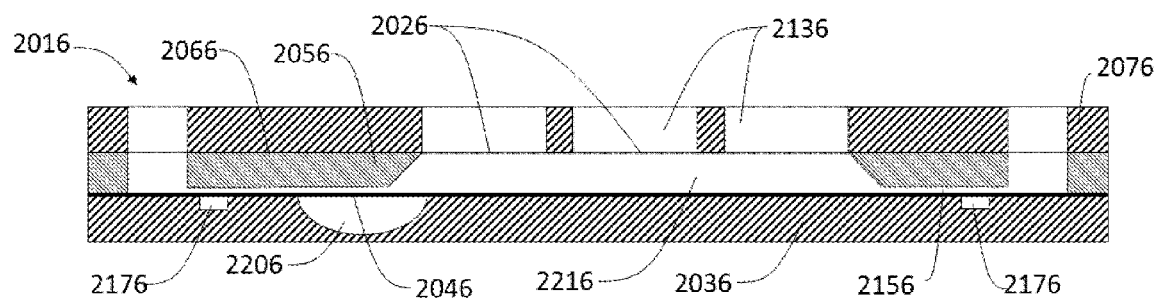
FIG. 6A shows a cross sectional view of a bioartificial organ device of a seventh embodiment of a device according to the invention having plural parallel access chambers associated to one single culturing chamber.

In FIG. 6A, a bioartificial organ device 2016 of a seventh embodiment of a device according to the invention is shown. The bioartificial organ device 2016 is principally similarly arranged as the bioartificial organ devices 201, 2010, 2019, 2018, 2017 described above. The bioartificial organ device 2016 includes a bottom body 2036 as a third body portion, with microvalves having microvalve chambers 2176 as well as with deflection actuation channels connected to deflection inlets on one side and to actuation chambers 2206 on the opposite side. On top of the bottom body 2036, an intermediate body 2056 with perfusion channels 2156 connected to perfusion inlets, culturing chambers 2216 and perfusion outlets is arranged as second body portion, wherein an actuation membrane 2046 is sandwiched between the bottom body 2036 and the intermediate body 2056. On top of the intermediate body 2056, a top body 2076 with perfusion inlet holes, access chambers 2136 and perfusion outlet holes is arranged as first body portion, wherein a thin porous culturing membrane 2066 is sandwiched between the intermediate body 2056 and the top body 2076. Sections of the culturing membrane 2066 being located in or below the access chambers 2136 of the top body 2076 form in-vitro barriers 2026. Each culturing chamber 2216 is associated to three access chambers 2136 and, thus, to three in-vitro barriers 2026. Also, each actuation chamber 2206 is associated to one culturing chamber 2216.

The aim of having plural in-vitro barriers 2026 per culturing chamber 2216 in the bioartificial organ device 2016 is to increase the overall surface of the in-vitro barrier 2026. In this embodiment, a group of in-vitro barriers 2026 is stretched simultaneously using a single actuation valve with an actuation chamber 2206. In this configuration, the pressure is distributed homogeneously in the cell culturing chamber 2216, allowing the in-vitro barriers 2026 to deflect simultaneously, with the microvalves having the valve chambers 217 that keep the culturing chamber 2216 closed.

Figure 6B:
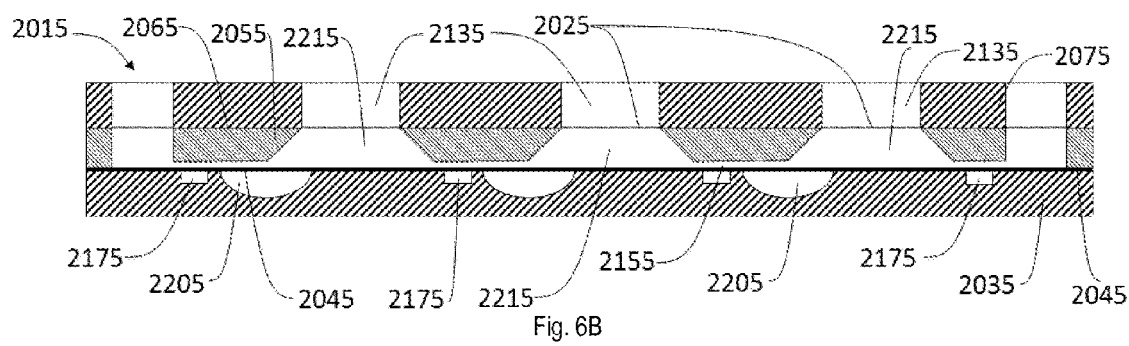
FIG. 6B shows a cross sectional view of a bioartificial organ device of an eighth embodiment of a device according to the invention having a series of culturing chambers and access chambers associated to one single perfusion channel.

FIG. 6B shows a bioartificial organ device 2015 of an eighth embodiment of a device according to the invention. The bioartificial organ device 2015 is principally similarly arranged as the bioartificial organ devices 201, 2010, 2019, 2018, 2017, 2016 described above. The bioartificial organ device 2015 includes a bottom body 2035 as a third body portion, with microvalves having microvalve chambers 2175 as well as with deflection actuation channels connected to deflection inlets on one side and to actuation chambers 2205 on the opposite side. On top of the bottom body 2035, an intermediate body 2055 with perfusion channels 2155 each being connected to perfusion inlets, three culturing chambers 2215 and perfusion outlets is arranged as second body portion, wherein an actuation membrane 2045 is sandwiched between the bottom body 2035 and the intermediate body 2055. On top of the intermediate body 2055, a top body 2075 with perfusion inlet holes, access chambers 2135 and perfusion outlet holes is arranged as first body portion, wherein a thin porous culturing membrane 2065 is sandwiched between the intermediate body 2055 and the top body 2075. Sections of the culturing membrane 2065 being located in or below the access chambers 2135 of the top body 2075 form in-vitro barriers 2025. Each perfusion culturing chamber 2215 is associated to one actuation chamber 2045 and to one valve chamber 2175.

Thus, the bioartificial organ device 2015 is equipped with groups of three in-vitro barriers 2025 that are actuated individually, each with a dedicated actuation valve or actuation chamber 2205, respectively. In this embodiment, the microvalve chambers 217 are located between the in-vitro barriers 2025 of a group so that each cell culturing chamber 2215 can be individually closed.

Figure 7A:
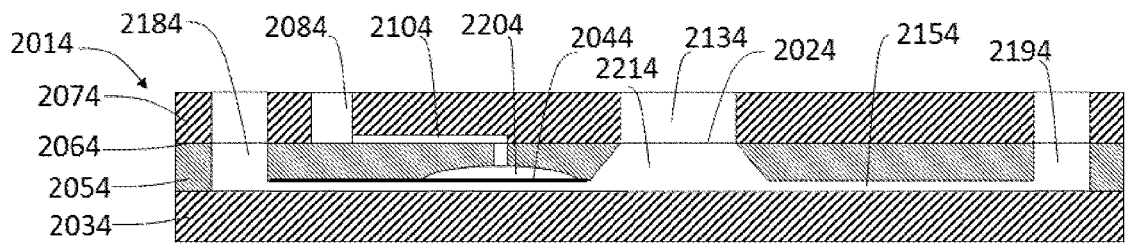
FIG. 7A shows a cross sectional view of a bioartificial organ device of a ninth embodiment of a device according to the invention having actuation chambers arranged in an intermediate body.
Figure 7B:
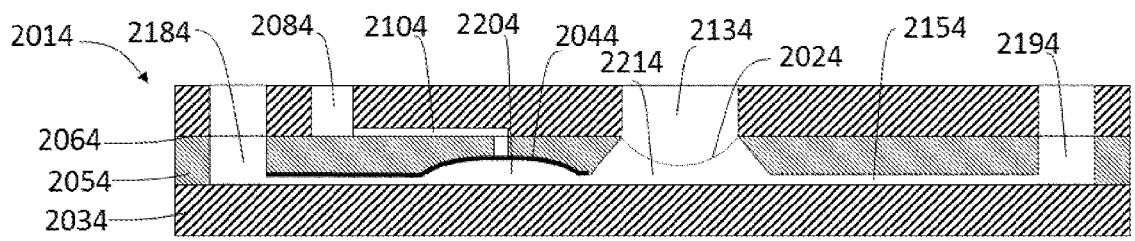
FIG. 7B shows a cross sectional view of the bioartificial organ device of FIG. 7A in a first deflected or actuated position.
Figure 7C:
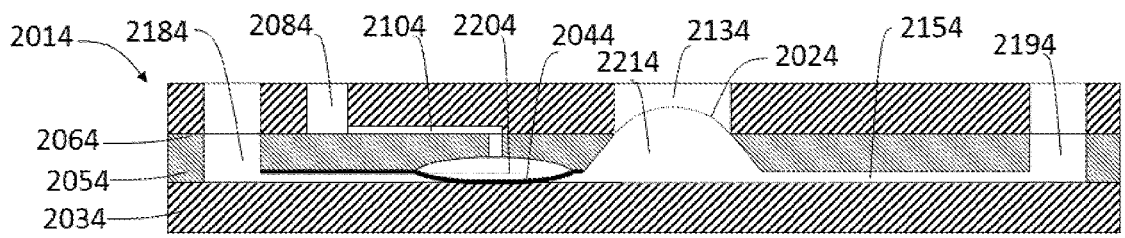
FIG. 7C shows a cross sectional view of the bioartificial organ device of FIG. 7A in a second deflected or actuated position.

FIGS. 7A, 7B, 7C show a bioartificial organ device 2014 of a ninth embodiment of a device according to the invention. The bioartificial organ device 2014 is principally similarly arranged as the bioartificial organ devices 201, 2010, 2019, 2018, 2017, 2016, 2015 described above. The bioartificial organ device 2014 includes a bottom body 2034 as fourth body portion, on top of which an intermediate body 2054 is arranged. The intermediate body 2054 has a second body portion of the bioartificial organ device 2014, with perfusion channels 2154 each connecting a perfusion inlet 2184 with a culturing chamber 2214 and a perfusion outlet 2194. The intermediate body 2054 further has a third body portion of the bioartificial organ device 2014, including end portions of deflection channels 2104 each passing over into an actuation chamber 2204 with a limitation cavity. The actuation chamber 2204 of the third body portion is located adjacent to the perfusion channel 2154 of the second body portion, between the perfusion inlet 2184 and the culturing chamber 2214. The actuation chamber 2204 is separated from the perfusion channel 2154 by an actuation membrane 2044. On top of the intermediate body 2054, a top body 2074 with perfusion inlet holes 2084, access chambers 2134, sections of the deflection channels 2104 and perfusion outlet holes is arranged as first body portion, wherein a thin porous culturing membrane 2064 is sandwiched between the intermediate body 2054 and the top body 2074. Sections of the culturing membrane 2064 being located in or below the access chambers 2134 of the top body 2074 form in-vitro barriers 2024.

Thus, in the bioartificial organ device 2014 the actuation chamber 2204 is arranged in the third body portion located in the intermediate body 2054. The actuation membrane 2044 is deflected via the deflection channel 2104. As illustrated in FIG. 7B, the actuation membrane 2044 can be upwardly or negatively deflected by a negative pressure in the deflection channel 2104. This causes the respective in-vitro barrier 2024 to deflect downwardly or into the culturing chamber 2214. Also, as illustrated in FIG. 7C, by applying a positive pressure in the deflection channel 2104 the actuation membrane 2044 can be downwardly or positively deflected. This causes the respective in-vitro barrier 2024 to be deflected upwardly or into the access chamber 2134. The in-vitro barrier 2024 can thus be efficiently strained positively, negatively or both positively and negatively.

In FIGS. 8A, 8B, 8C and 8D, a fabrication of a thin porous culturing membrane 206x, as it can be implemented in any of the embodiments of bioartificial organ devices described above, is shown. The culturing membrane 206x can be made of a material with a plurality of pores 801, wherein molecules, cells, fluid or any other media is capable of passing though the thin porous culturing membrane 206x via one or more pores 801. As discussed below in more detail, the thin porous culturing membrane 206x is made of a material that allows undergoing stress and/or strain in response to pressure differentials present between the cell culturing chamber and the pressure surrounding the bioartificial organ device. The thickness of the thin porous culturing membrane 206x is between about 20 nanometers and about 20 micrometers, and preferably is between about 200 nanometers and about 5 micrometers. The size of the pores 801 is between about 0.4 micrometers and about 12 micrometers, and preferably is at about 3 micrometers. The density of the pores is between about 10'000 and about 100'000'000 pores/cm$^2$, and preferably is at about 800'000 pores/cm$^2$. It is also contemplated that the in-vitro barrier can be equipped with a non-porous membrane.

Figure 8A:
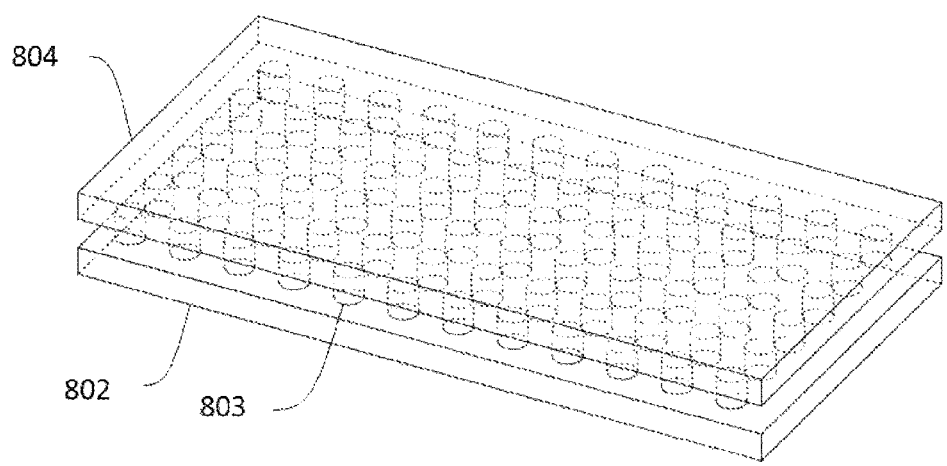
FIG. 8A shows a perspective view of a device for fabricating a thin porous culturing membrane.
Figure 8B:
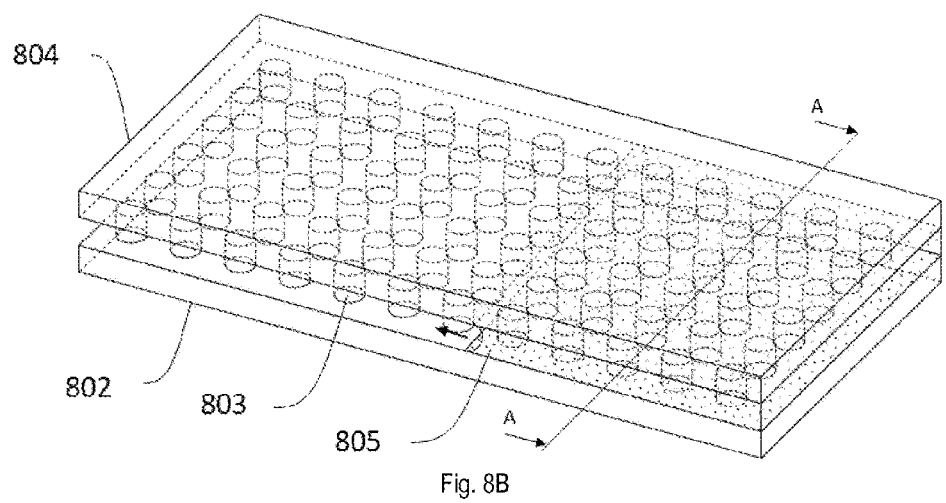
FIG. 8B shows a perspective view of the device of FIG. 8A while being loaded.
Figure 8C:
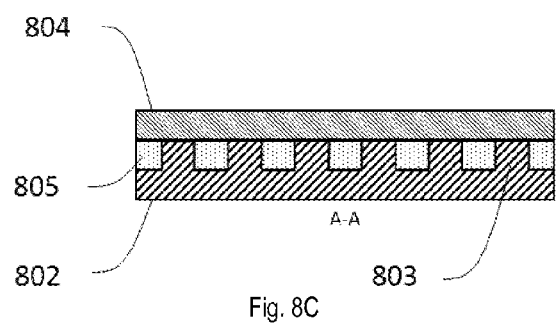
FIG. 8C shows a cross sectional view along line A-A of the perspective view of FIG. 8B.
Figure 8D:
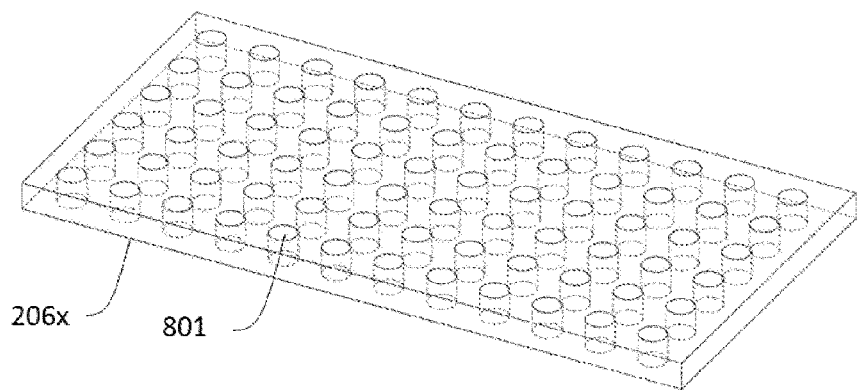
FIG. 8D shows a perspective view of a culturing membrane fabricated with the device of FIG. 8A.

FIGS. 8A, 8B and 8C show the schematic fabrication process of the thin porous culturing membrane 206x with possible geometries of the membrane holes 801. A mold 802 with an array of micropillars 803 is covered by a covering substrate 804. A non-polymerized fluid 805 is passively introduced by capillary forces or pressed by force in the empty space created between the mold 802, the covering substrate 804 and the array of micropillars 803 (see FIG. 8B). FIG. 8C illustrates the cross-section of the assembly of the mold 802 and the covering substrate 804 with the spaces filled with the non-polymerized fluid 805. The height of the micropillars 803 defines the thickness of the non-polymerized fluid 805. Curing the non-polymerized fluid 805, for a set temperature and time, produces the thin culturing membrane 206x having an array of pores 801 (FIG. 8D). In an embodiment, the mold 802 can be fabricated by wet or dry etching of silicon, silicon dioxide, silicon nitride or the like.

Figure 9A:
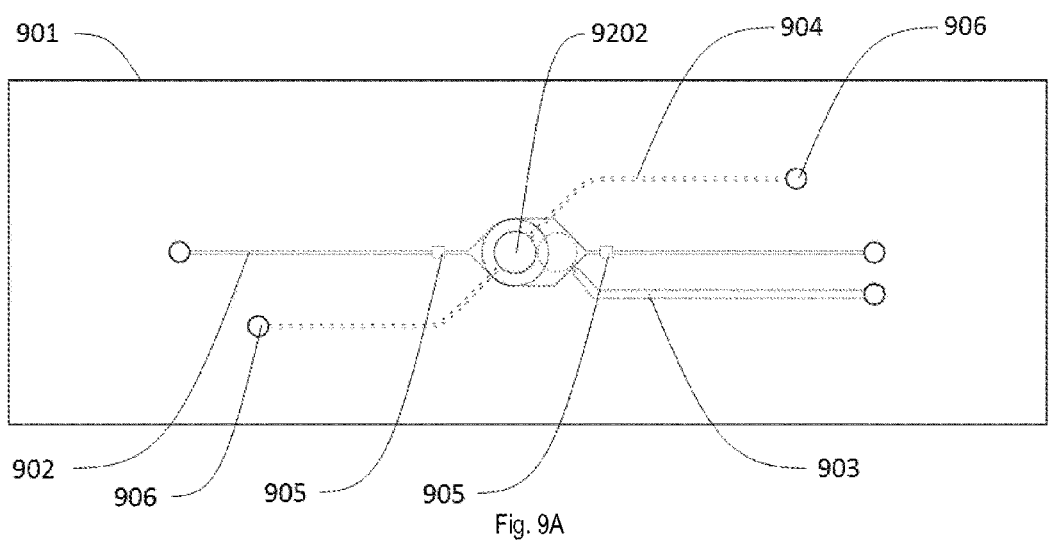
FIG. 9A shows a top view on a bioartificial organ device of a tenth embodiment of a device according to the invention.
Figure 9B:
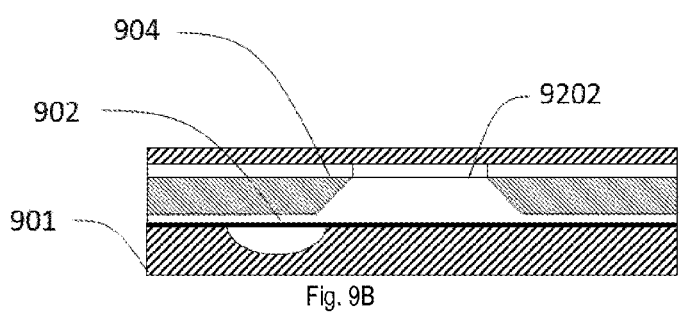
FIG. 9B shows a cross sectional view of the bioartificial organ device of FIG. 9A.

FIGS. 9A and 9B show a bioartificial organ device 901 of a tenth embodiment of a device according to the invention in a top view and a cross sectional view. In the bioartificial organ device 901, the in-vitro barrier 9202 can be perfused on both sides. A perfusion channel 904 is connected to the top side of the in-vitro-barrier 9202 via the in-vitro barrier access ports and one perfusion channel 902 to its bottom side. FIG. 9B illustrates a detailed view of the cross-section of the bioartificial organ device 901 in this possible embodiment. It is contemplated that several perfusion channels 904 are connected to the in-vitro barrier 9202.

Figure 10:
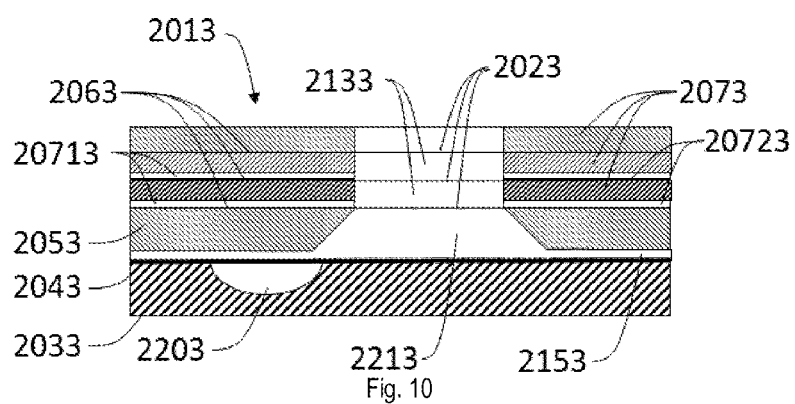
FIG. 10 shows a cross sectional view of a bioartificial organ device of an eleventh embodiment of a device according to the invention having plural vertically spaced access chambers associated to one single culturing chamber.

In FIG. 10, a bioartificial organ device 2013 of an eleventh embodiment of a device according to the invention is shown. The bioartificial organ device 2013 is principally similarly arranged as the bioartificial organ devices 201, 901, 2010, 2019, 2018, 2017, 2016, 2015, 2014 described above. The bioartificial organ device 2013 includes a bottom body 2033 as a third body portion, with actuation chambers 2203. On top of the bottom body 2033, an intermediate body 2053 with perfusion channels 2153 each being connected to a perfusion inlet, a culturing chamber 2213 and a perfusion outlet is arranged as second body portion, wherein an actuation membrane 2043 is sandwiched between the bottom body 2033 and the intermediate body 2053. On top of the intermediate body 2053, three top bodies 2073 each with an access chamber 2133 are arranged as first body portion, wherein thin porous or non-porous culturing membranes 2063 are sandwiched between the intermediate body 2053 and the top bodies 2073, as well as between the top bodies 2073. Sections of the culturing membranes 2063 being located in or below the access chambers 2133 of the top body 2073 form in-vitro barriers 2023. Each of the top body 2073 between the intermediate body 2053 and the next top body 2073, as well as the top body 2073 between the two other top bodies 2073, is equipped with an access chamber inlet channel 20713 and an access chamber outlet channel 20723 for providing a medium to and from the respective access chamber 2133.

FIGS. 11A, 11B, 11C and 11D show a bioartificial organ device 2012 of a twelfth embodiment of a device according to the invention. The bioartificial organ device 2012 is principally similarly arranged as the bioartificial organ devices 201, 901, 2010, 2019, 2018, 2017, 2016, 2015, 2014, 2013 described above. The bioartificial organ device 2012 includes a bottom body 2032 as a third body portion, with microvalves having microvalve chambers 2172 as well as with deflection actuation channels 2102 connected to deflection inlets on one side and to actuation chambers 2202 on the opposite side. On top of the bottom body 2032, an actuation membrane 2042 covering the bottom body 2032 is mounted. The bioartificial organ device 2012 further includes an intermediate body 2052 with perfusion channels 2152 connected to perfusion inlets 21512, culturing chambers 2212 and perfusion outlets 21522 as second body portion. On top of the intermediate body 2052, a top body 2072 with perfusion inlet holes, access chambers 2132 and perfusion outlet holes is arranged as first body portion, wherein a thin porous culturing membrane 2062 is sandwiched between the intermediate body 2052 and the top body 2072. Sections of the culturing membrane 2062 being located in or below the access chambers 2132 of the top body 2072 form in-vitro barriers 2022. The bioartificial organ device 2012 is adapted such that the bottom body 2032 and the actuation membrane 2042 can be removed as a bottom part from the intermediate body 2052, the culturing membrane 2062 and the top body 2072 as a top part.

Figure 11A:
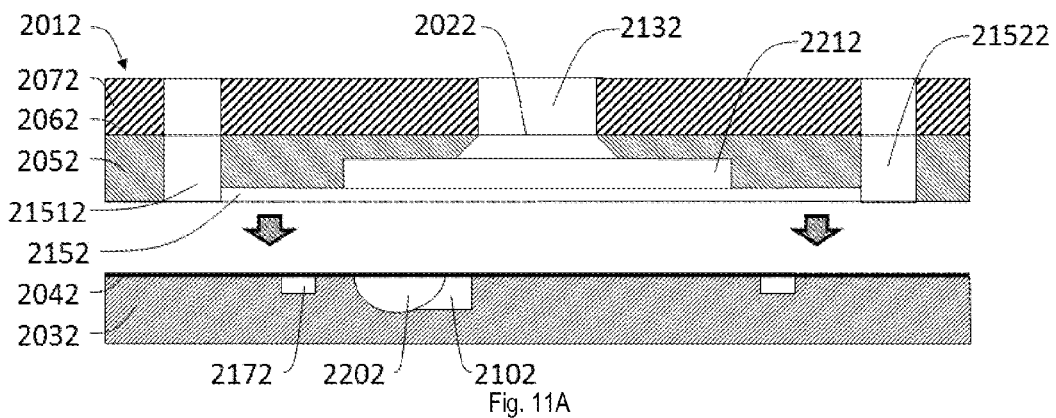
FIG. 11A shows a cross sectional view of a bioartificial organ device of a twelfth embodiment of a device according to the invention arranged for growing cells on both sides of a culturing membrane.
Figure 11B:
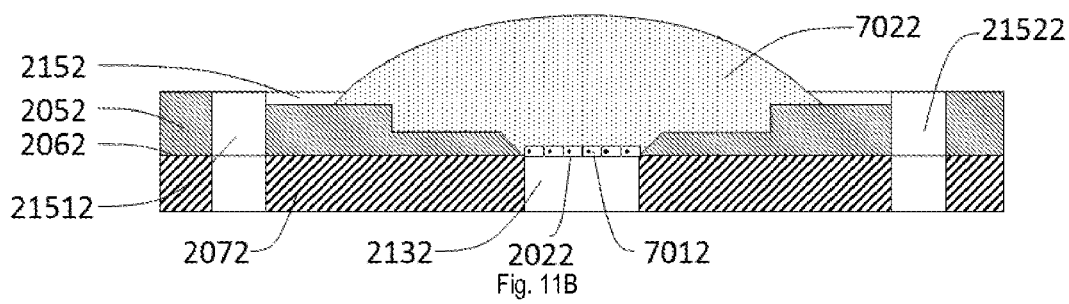
FIG. 11B shows a cross sectional view of the bioartificial organ device of FIG. 11A while cells are grown on one side of the culturing membrane.
Figure 11C:
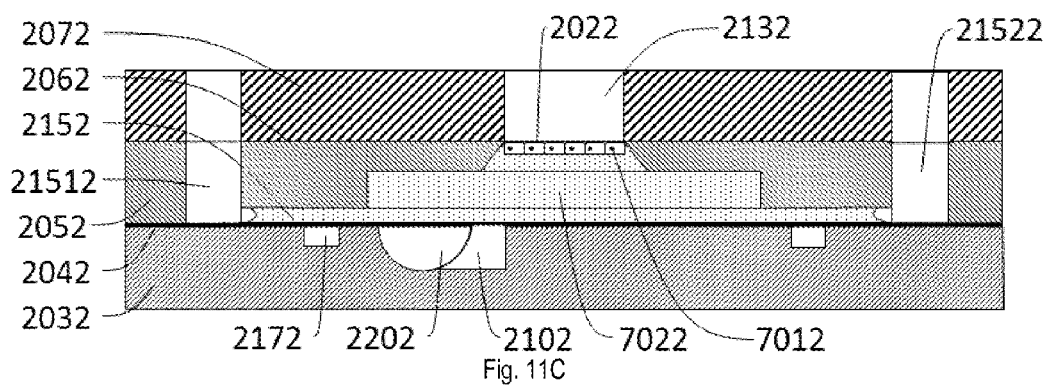
FIG. 11C shows a cross sectional view of the bioartificial organ device of FIG. 11A being reassembled.
Figure 11D:
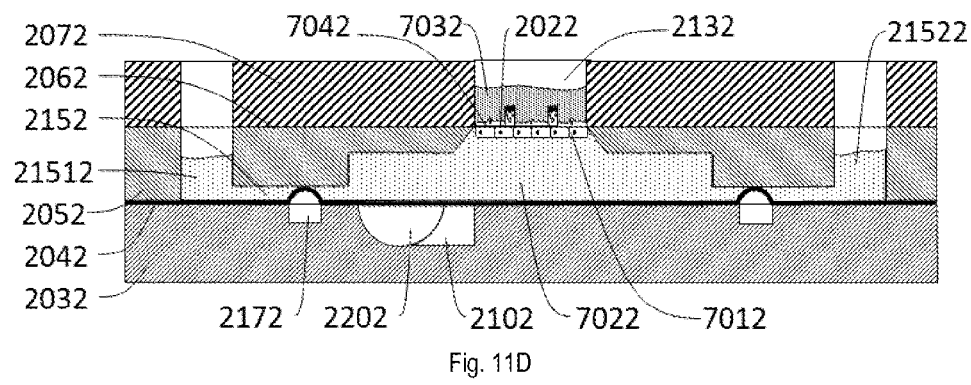
FIG. 11D shows a cross sectional view of the bioartificial organ device of FIG. 11A while cells are grown on a second side of the culturing membrane.

In use, as shown in FIG. 11B, the intermediate body 2052, the culturing membrane 2062 and the top body 2072 are flipped by 180° and a culturing medium 7022 is dropped in the culturing chamber 2212. Thus, the culturing medium 7022 containing cells and/or other cellular aggregates in suspension, is loaded on the backside of the culturing membrane 2062 and cells 7012 grow and form an in-vitro barrier 2022. The cells 7012 are thus loaded on the backside of the culturing membrane 2062 with the bioartificial organ device 2012 turned upside down. As shown in FIG. 11C, once the cells adhere to the culturing membrane 2062, the intermediate body 2052, the culturing membrane 2062 and the top body 2072 is turned down and assembled with the bottom body 2032 and the actuation membrane 2042. Both parts can be assembled using a holder using mechanic, electric, magnetic forces or a combination thereof. The culturing medium 7022 is then squeezed between the two bodies and guided via the perfusion channels 2152. As shown in FIG. 11D, once assembled, additional cells 7042 provided in a culturing medium 7032 can be loaded and cultured on the upper side of the culturing membrane 2062, inside the access chamber 2132. As described earlier, the microvalves are closed prior to activating the actuation of the culturing membrane 2062. The fluid is trapped between the body parts and in the culturing chamber 2132 that has a volume large enough for the cells to survive for at least the period of the assay. Typically, the volume of the culturing chamber 2212 is about 50 microliters, but can be between about 0.5 microliters and about 500 microliters. The excess of fluid is directed towards a fluid exit chamber in which the fluid overflows. It is contemplated that the bioartificial organ device 2012 can be opened and closed again to repeat the process described above, in order to load additional cell type, molecules, nanoparticles.

Figure 11E:
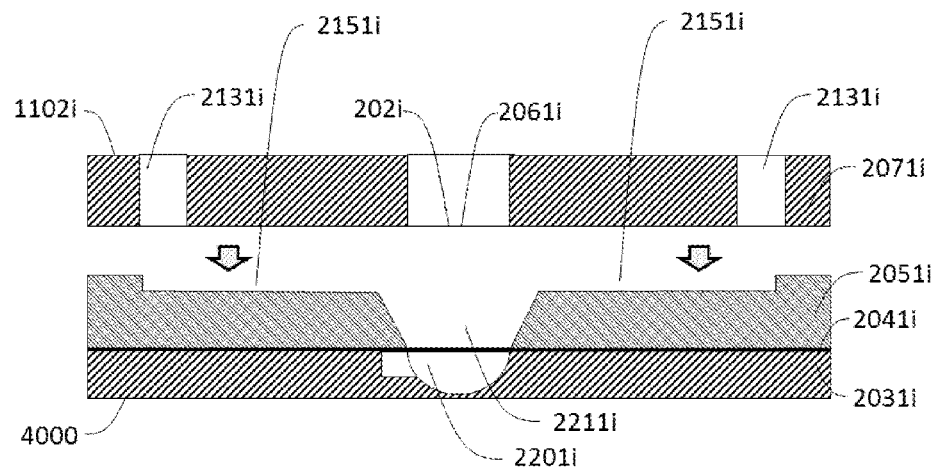
FIG. 11E shows a cross sectional view of a bioartificial organ device of a thirteenth embodiment of a device according to the invention arranged for growing cells on both sides of a culturing membrane.

In FIG. 11E, a bioartificial organ device 4000 of a thirteenth embodiment of a device according to the invention is shown. The bioartificial organ device 4000 is principally similarly arranged as the bioartificial organ devices 201, 901, 2010, 2019, 2018, 2017, 2016, 2015, 2014, 2013, 2012, 2011 described above. The bioartificial organ device 4000 includes a bottom body 2031$i$ as a third body portion, with deflection actuation channels connected to deflection inlets on one side and to actuation chambers 2201$i$ on the opposite side. On top of the bottom body 2031$i$, an intermediate body 2051$i$ with perfusion channels 2151$i$ connected culturing chambers 2211$i$ is arranged as second body portion, wherein an actuation membrane 2041$i$ is sandwiched between the bottom body 2031$i$ and the intermediate body 2051$i$. On top of the intermediate body 2051$i$, a top body 2071$i$ with access chambers 2131$i$ is arranged as first body portion, wherein a thin porous culturing membrane 2061$i$ is sandwiched between the intermediate body 2051$i$ and the top body 2071$i$. Sections of the culturing membrane 2061$i$ being located in or below the access chambers 2131$i$ of the top body 2071$i$ form in-vitro barriers 2021$i$. In this embodiment, the perfusion channels 2151$i$ are cavities in the intermediate body 2051$i$ that are closed once the top body 2071$i$ is assembled with the intermediate body 2051$i$. The assembly between the top body 2071$i$ on which the culturing membrane 2061$i$ is attached is reversible. The assembly can be used to load one or several drops of cell culture medium with suspended cells, prior to being assembled.

The reversible bonding is used to load cells on the bioartificial organ device or to sample cell supernatant for further analysis or to observe cells on the culturing membrane or to add cell culture medium or other substances. For the implementation of the reversible bonding, one or two body parts of the bioartificial organ device need to be equipped with one or several cavities that, once assembled with the second body part, enable the creation of a cell culture chamber.

Other body parts of the bioartificial organ device can be reversibly bonded for the same or other purposes. It is envisaged that the top body part may be reversibly assembled with the intermediate body part.

The reversible bonding system also allows creation of microvalves using body parts that can reversibly be assembled, cleaned, surface treated to render them hydrophilic and hydrophobic.

In an embodiment, a drop of culturing medium with suspended cells is placed on top of the bottom body 2032i. The top body is then immediately bonded to the lower body with methods explained earlier and flipped by 180° to allow the cells to adhere on the culturing membrane 2062i. Once the cells are adhered, the bioartificial organ device is flipped again and cells cultured at the top of the culturing membrane.

In an embodiment, a drop of culturing medium without suspended cells is placed on top of the bottom body 2032i. The top body is then immediately bonded to the lower body with methods explained earlier and cells added at the top of the culturing membrane. Such embodiment would be interesting to study cells only on the top of the culturing membrane 2062i.

Figure 12A:
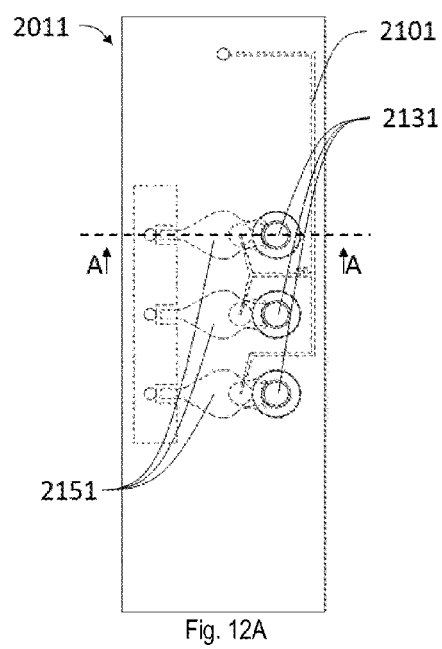
FIG. 12A shows a top view of a bioartificial organ device of a fourteenth embodiment of a device according to the invention having a closable culturing chamber.
Figure 12B:
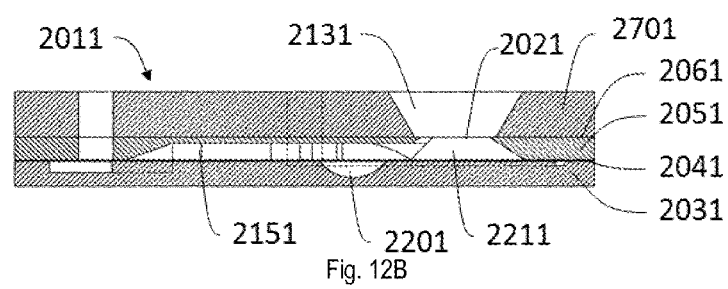
FIG. 12B shows a cross sectional view along the line A-A of the top view of FIG. 12A.

In FIGS. 12A and 12B, a bioartificial organ device 2011 of a fourteenth embodiment of a device according to the invention is shown. The bioartificial organ device 2011 is principally similarly arranged as the bioartificial organ devices 201, 901, 2010, 2019, 2018, 2017, 2016, 2015, 2014, 2013, 2012 described above. The bioartificial organ device 2011 includes a bottom body 2031 as a third body portion, with deflection actuation channels connected to deflection inlets on one side and to actuation chambers 2201 on the opposite side. On top of the bottom body 2031, an intermediate body 2051 with perfusion channels 2151 connected culturing chambers 2211 is arranged as second body portion, wherein an actuation membrane 2041 is sandwiched between the bottom body 2031 and the intermediate body 2051. On top of the intermediate body 2051, a top body 2071 with access chambers 2131 is arranged as first body portion, wherein a thin porous culturing membrane 2061 is sandwiched between the intermediate body 2051 and the top body 2071. Sections of the culturing membrane 2061 being located in or below the access chambers 2131 of the top body 2071 form in-vitro barriers 2021. The bioartificial organ device 2011 is equipped with means for closing the culturing chamber 2211. As shown in FIG. 12, the culturing chamber 2211 is closed once cells are seeded on the bottom side of the culturing membrane 2061.

Figure 13A:
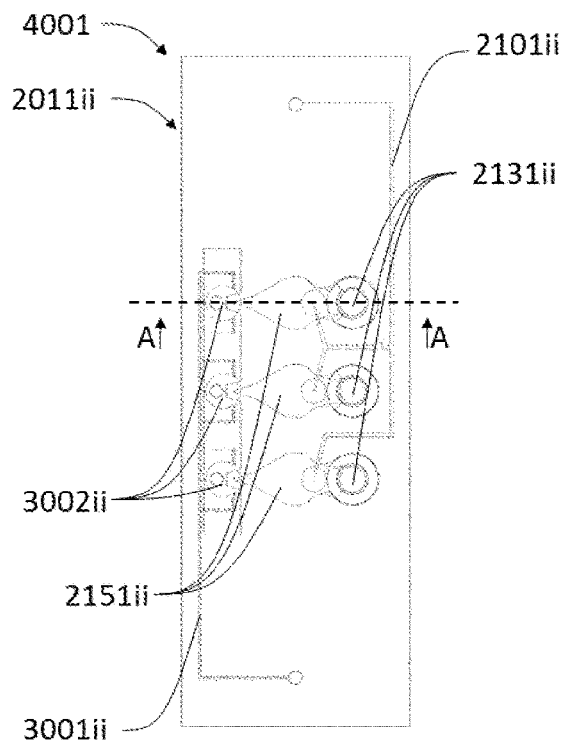
FIG. 13A shows a top view of a bioartificial organ device of a fifteenth embodiment of a device according to the invention having a microvalve that closes a culturing chamber and equilibrates a culturing membrane.
Figure 13B:
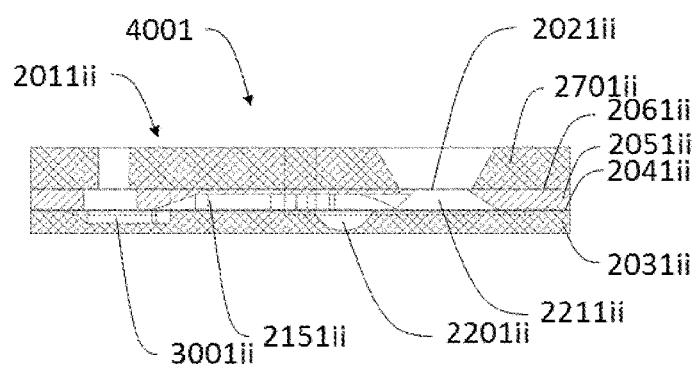
FIG. 13B shows a cross sectional view along the line A-A of the top view of FIG. 13A.

In FIG. 13A and FIG. 13B, a bioartificial organ device 4001 of a fifteenth embodiment of a device according to the invention is shown. The bioartificial organ device 4001 is principally similarly arranged as the bioartificial organ devices 201, 901, 2010, 2019, 2018, 2017, 2016, 2015, 2014, 2013, 2012, 2011 described above. The bioartificial organ device 4001 includes a bottom body 2031ii as a third body portion, with deflection actuation channels connected to deflection inlets on one side and to actuation chambers 2201ii on the opposite side. On top of the bottom body 2031ii, an intermediate body 2051ii with perfusion channels 2151ii connected culturing chambers 2211ii is arranged as second body portion, wherein an actuation membrane 2041ii is sandwiched between the bottom body 2031ii and the intermediate body 2051ii. On top of the intermediate body 2051ii, a top body 2071ii with access chambers 2131ii is arranged as first body portion, wherein a thin porous culturing membrane 2061ii is sandwiched between the intermediate body 2051ii and the top body 2071ii. Sections of the culturing membrane 2061ii being located in or below the access chambers 2131ii of the top body 2071ii form in-vitro barriers 2021ii. In this embodiment, the bioartificial organ device 4001 is equipped with a normally closed microvalve 3002ii for closing the culturing chamber 2211ii. This microvalve 3002ii allows calibration of the thin porous membrane 2021ii, by equilibrating the pressures on both sides of the thin porous membrane 2021ii. Indeed, after closing the culturing chamber 2211ii, the thin porous membrane 2021ii may slightly be inflated due to the excess of culturing medium contained in the hanging drop. Prior to the closing of the culturing chamber 2211ii, the actuation membrane 2041ii is deflected by applying a negative pressure in the actuation channel 3001ii. Once the intermediate part 2051ii including the thin, porous membrane 2021ii, is aligned and attached to the bottom part 2031ii, the negative pressure is shut off in the actuation channel 3001ii that releases the actuation membrane 2041ii and closes the microvalve 3002ii. The design of the microvalve 3002ii is conceived so that a minimum of the culturing medium enters in the perfusion channel 2151ii and the culturing chamber when the microvalve 3002ii closes.

Figure 14:
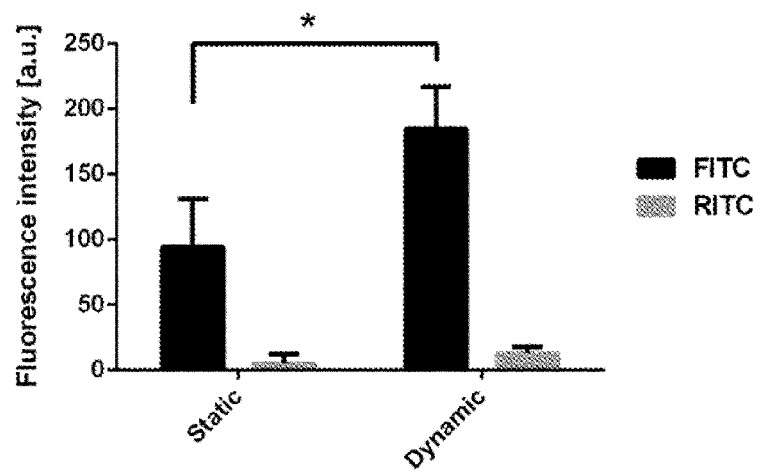
FIG. 14 shows the effects of a cyclic mechanical strain (10% linear) on the permeability of an epithelial barrier.

FIG. 14 illustrates the effects of a physiologic (10% linear), cyclic mechanical strain on the permeability of an epithelial barrier. Lung bronchial epithelial cells (16HBEo-) were seeded at a density of 250'000 cells/cm$^2$ onto the fibronectin-coated culturing membrane. The cells were allowed to adhere and to grow for 72 h. The cells were exposed to cyclic strain (10% linear, 0.2 Hz) for 19 h, whereas the control was kept at static conditions. Cell permeability was measured using two molecules, FITC-sodium and RITC-Dextran. After 2 h of incubation, the permeability of each molecule was measured with a fluorescence multiplate reader (Tecan Infinite M1000; Ex:460/Em:515 & Ex:553/Em:627). The results show that cells that were stretched for 19 h present a significantly increased transmembrane permeability to the small molecule (FITC-sodium) compared to control cells in static conditions. In contrast, no significant permeability differences were observed for the large molecule (RITC-Dextran) between an epithelial cell layer that was stretched or not. The importance of the cyclic mechanical strain on the air-blood barrier permeability is clearly demonstrated in this clinically relevant experiment that may predict the type of molecules entering in the blood stream via the inhalation route.

Figure 15:
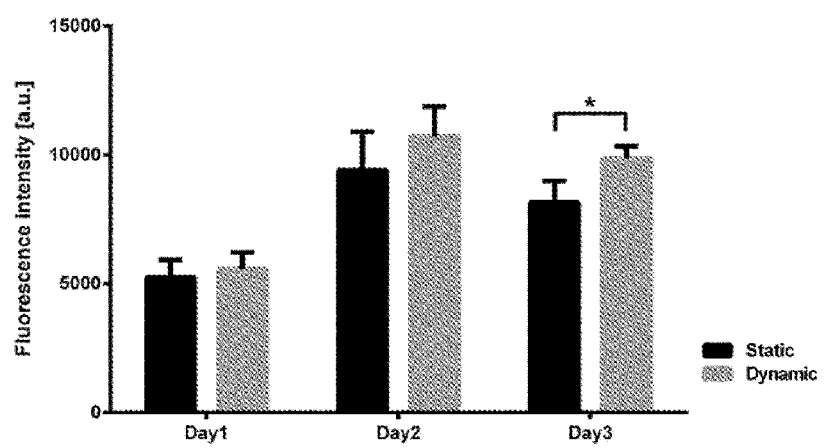
FIG. 15 shows the effects of a cyclic mechanical strain (10% linear) on the metabolic activity of human primary alveolar epithelial cells.

FIG. 15 illustrates the effects of a physiologic, cyclic mechanical strain on the metabolic activity of a confluent layer of primary human alveolar epithelial cells. In this experiment, primary human alveolar epithelial cells were seeded at a density of 400,000 cells/cm$^2$ onto the gelatin/collagen1-coated actuation membrane. The cells were allowed to adhere and to grow for 48 h. The cells were exposed to cyclic strain (10% linear, 0.2 Hz) for 48 h, whereas the control was kept at static conditions for the same period of time. Cell vitality and proliferation were measured using the non-toxic AlamarBlue assay (Invitrogen) 1 h before applying the cyclic stretch, and 23 h and 47 h after starting to stretch the cells. During the incubation of 1 h, all cells were kept at static condition. After incubation, the reduced form of AlamarBlue was measured with a fluorescence multiplate reader (Tecan Infinite M1000; Ex:570/Em:585). The results show that cells that were stretched for 48 h have a significantly increased metabolic activity compared to control cells that did not undergo mechanical stimulation.

With the embodiments of devices shown in the present disclosure, it is intended to describe and produce a high-throughput lung-on-chip system compatible with standard robotic pipetting stations used in the pharmaceutical industry (drug discovery process). Microfluidic systems are in general well suited for such implementation. However, one of the challenges of an in-vitro barrier system like the one described is the culture of the cells at the bottom of the culturing membrane. This requires flipping the platform in order to allow the cells to adhere on the membrane (otherwise they would sediment at the bottom of the system). Instead of using a microfluidic channel to load the cells in the system and flipping the plate once the cells are introduced, it is preferred to flip the plate first and add a drop of medium with suspended cells on the culturing membrane and let them adhere. In contrast to the cell seeding via a channel, in which the cells adhere, this solution presents the important advantage that the number of cells seeded on the membrane is well known. Then the system is closed (without air bubbles) and used either in a perfused or a non-perfused mode.

With the embodiments of devices shown in the present disclosure, it is intended to describe and produce a high-throughput lung-on-chip system compatible with exposure systems for in vitro studies of gases, complex mixtures, fibers, nanoparticles to study the effects of airborne substances. Such systems allow reproducing the exposure of the lung airways to all kinds of particles that are inhaled. It is therefore envisaged to expose the cells (primary and/or cells lines for instance from the respiratory tract), cultured on this device to direct contact between cells and components of the test atmosphere, either at the air-liquid interface or to the solution in which the cells are cultured. Applications of such systems are in the investigation of the toxicity and functionality of drugs (for instance respiratory drugs) or the toxicity of various substances from combustion processes (exhaust), cosmetics, household chemicals, industrial chemicals, pesticides, insecticides, other pharmaceuticals, tobacco smoke, and could also be used to perform indoors and outdoors air analysis.

In a non-perfused system being closed (static physiological solution), there should be enough nutrients for the cells to survive during the time of the assay. The lower part can be made of a recess located around the culturing membrane that will contain the medium once assembled. In addition, a system allowing for the excess of solution to flow out of the culturing chamber is implemented so that no air bubbles can be contained in the system. Two solutions are envisaged, the first is made of a valve and the second without valve. In both cases, one needs to make sure that the culturing membrane is not deflected when the system is closed. The culturing chamber made of the recess closed by the body portion can have a volume of about 50 µL and can be in the range of about 10 µL to about 200 µL. In a perfused system, the volume of the recess does not need to be as large and can be reduced to a few microliters.

For closing the system, either permanently or non-permanently, several solutions can be envisaged. The possibility of disassembling the system can allow further analysis of the cells (lysis, RT-PCR or the like). In one embodiment, a holder maintains the two body parts together, with a mechanical force generated by a spring, or an attachment means, such as screws or the like. It could also be envisaged that the two parts would be assembled using specific pins in the top or bottom parts that would be clipped in the other part.

While the invention has been illustrated and described in detail in the drawings and foregoing description, such illustration and description are to be considered illustrative or exemplary and not restrictive. It will be understood that changes and modifications may be made by those of ordinary skill within the scope and spirit of the following claims. In particular, the present invention covers further embodiments with any combination of features from different embodiments described above and below.

The invention also covers all further features shown in the figures individually although they may not have been described in the afore or following description. Also, single alternatives of the embodiments described in the figures and the description and single alternatives of features thereof can be disclaimed from the subject matter of the invention or from disclosed subject matter. The disclosure includes subject matter consisting of the features defined in the claims or the exemplary embodiments as well as subject matter including these features.

Furthermore, in the claims the word "comprising" does not exclude other elements or steps, and the indefinite article "a" or "an" does not exclude a plurality. A single unit or step may fulfill the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Any reference signs in the claims should not be construed as limiting the scope.

The invention claimed is:

1. A method of using a device for in-vitro modelling in-vivo tissues of organs, the device comprising a first body portion with a vertical through-hole forming at least one access chamber, a second body portion with a vertical through-hole forming at least one culturing chamber, and a culturing membrane dividing the at least one access chamber from the culturing chamber, the method comprising:
    incubating cells by downwardly placing a drop of a culturing medium via the vertical through-hole of a first one of the first body portion and the second body portion on top of a first side of the culturing membrane;
    flipping the first body portion and the second body portion together with the culturing membrane by about 180°; and
    incubating further cells by downwardly placing a drop of a further culture medium via the vertical through-hole of a second one of the first body portion and the second body portion on top of a second side of the culturing membrane, wherein the culture medium comprises cells attaching to the first side of the culturing membrane when incubating the cells and/or the further culture medium comprises further cells attaching to the second side of the culturing membrane when incubating the further cells.

2. The method of claim 1, wherein the device further comprises a perfusion channel with an inlet, an outlet, and the at least one culturing chamber, wherein the inlet, the at least one culturing chamber, and the outlet are connected.

3. The method of claim 2, wherein incubating the cells on the first side of the culturing membrane comprises providing the cells through the inlet of the perfusion channel into the culturing chamber.

4. The method of claim 3, wherein at least one of growth factors, chemicals, gases, nutrients drugs, xenobiotics, blood, or blood serum is provided through the inlet of the perfusion channel into the culturing chamber together with the cells.

5. The method of claim 2, wherein incubating the further cells on the second side of the culturing membrane comprises providing the further cells into the access chamber.

6. The method of claim 5, wherein at least one of growth factors, chemicals, gases, nutrients drugs, xenobiotics, blood or blood serum is provided into the access chamber together with the further cells.

7. The method of claim 1, wherein the device further comprises a third body portion.

8. The method of claim 7, wherein the third body portion comprises at least one actuation chamber with at least one limitation cavity, and an actuation membrane dividing the at least one culturing chamber from the at least one actuation chamber, wherein the method comprises actuating the culturing membrane by moving the actuation membrane.

9. The method of claim 7, wherein the method comprises assembling the third body portion to the first body portion and the second body portion after flipping the first body portion and the second body portion together with the culturing membrane by about 180°.

10. The method of claim 7, wherein the third body portion is assembled to the first body portion and the second body portion using a holder that uses a mechanic force, an electric force, a magnetic force, or a combination thereof.

11. The method of claim 7, wherein the third body portion defines a closed culturing chamber limited by the culturing membrane.

12. The method of claim 1, wherein the culturing membrane is porous.

13. The method of claim 1, wherein the first side of the culturing membrane is opposite to the second side of the culturing membrane.

* * * * *